US011542467B2

(12) United States Patent
Gerritzen et al.

(10) Patent No.: US 11,542,467 B2
(45) Date of Patent: Jan. 3, 2023

(54) PROCESS FOR PRODUCING OUTER MEMBRANE VESICLES

(71) Applicant: De Staat der Nederlanden, vert. door de minister van VWS, Ministerie van Volksgezondheid, Welzijn en Sport, The Hague (NL)

(72) Inventors: Matthias Joannes Hendrikus Gerritzen, Eindhoven (NL); Leonardus Aldolfus van der Pol, Groningen (NL); Michiel Stork, Zeist (NL)

(73) Assignee: Intravacc B.V., Bilthoven (NL)

( * ) Notice: Subject to any disclaimer, the term of this patent is extended or adjusted under 35 U.S.C. 154(b) by 70 days.

(21) Appl. No.: 16/768,919

(22) PCT Filed: Dec. 4, 2018

(86) PCT No.: PCT/EP2018/083448
§ 371 (c)(1),
(2) Date: Jun. 2, 2020

(87) PCT Pub. No.: WO2019/110569
PCT Pub. Date: Jun. 13, 2019

(65) Prior Publication Data
US 2021/0238540 A1 Aug. 5, 2021

(30) Foreign Application Priority Data

Dec. 4, 2017 (EP) ..................................... 17205138

(51) Int. Cl.
*C12N 1/20* (2006.01)
*A61K 39/02* (2006.01)
*A61K 39/09* (2006.01)
*A61K 39/108* (2006.01)
*A61K 39/00* (2006.01)

(52) U.S. Cl.
CPC ............ *C12N 1/20* (2013.01); *A61K 39/0258* (2013.01); *A61K 39/099* (2013.01); *A61K 2039/55555* (2013.01)

(58) Field of Classification Search
None
See application file for complete search history.

(56) References Cited

U.S. PATENT DOCUMENTS

2014/0147469 A1* 5/2014 Van De Waterbeemd ..................
A61P 39/00
424/234.1

FOREIGN PATENT DOCUMENTS

| EP | 1905839 A1 | 4/2008 |
| WO | WO2006/046143 A2 | 5/2006 |
| WO | WO2011/036562 A1 | 3/2011 |
| WO | WO2012/097185 A2 | 7/2012 |
| WO | WO2013/006055 A1 | 1/2013 |

OTHER PUBLICATIONS

Van De Waterbeemd B. et al: Cysteine Depletion Causes Oxidative Stress and Triggers Outer Membrane Vesicle Release by Neisseria meningitidis; Implications for Vaccine Development, PLOS ONE. vol. 8, No. 1, E54314, Jan. 23, 2013, pp. 1-10.
Baart G. J. E. et al.: Scale-up for bulk production of vaccine against meningococcal disease, Vaccine, vol. 25, No. 34, Jun. 26, 2007, pp. 6399-6408.
Van Der Pol L. et al: Outer membrane vesicles as platform vaccine technology, Biotechnology Journal, vol. 10, No. 11, Sep. 1, 2015, pp. 1689-1706.
Schwechheimer C. et al: "Outer-membrane vesicles from Gram-negative bacteria: biogenesis and functions", Nature Reviews. Microbiology, vol. 13, No. 10, Sep. 16, 2015, pp. 605-619.
Gerritzen M. J. H. et al: Bioengineering bacterial outer membrane vesicles as vaccine platform, Biotechnology Advances, vol. 35, No. 5, May 15, 2017, pp. 565-574.
Sabra W. et al: "Alterations in the formation of lipopolysaccharide and membrane vesicles on the surface of Pseudomonas aeruginosa PA01 under oxygen stress conditions", Microbiology, vol. 149, No. 10, Oct. 1, 2003, pp. 2789-2795.
Alves NJ, Turner KB, Daniele MA, Oh E, Medintz IL, Walper SA. 2015. Bacterial Nanobioreactors—Directing Enzyme Packaging into Bacterial Outer Membrane Vesicles. ACS Appl Mater Interfaces 7(44):24963-72.
Archibald FS, Duong MN. 1986. Superoxide dismutase and oxygen toxicity defenses in the genus *Neisseria*. Infect Immun 51(2):631-41.
Aspholm M, Aas FE, Harrison OB, Quinn D, Vik A, Viburiene R, Tonjum T, Moir J, Maiden MC, Koomey M. 2010. Structural alterations in a component of cytochrome c oxidase and molecular evolution of pathogenic Neisseria in humans. PLoS Pathog 6(8):e1001055.
Baart GJ, Zomer B, de Haan A, van der Pol LA, Beuvery EC, Tramper J, Martens DE. 2007b. Modeling Neisseria meningitidis metabolism: from genome to metabolic fluxes. Genome Biol 8(7):R136.
Baez A, Shiloach J. 2014. Effect of elevated oxygen concentration on bacteria, yeasts, and cells propagated for production of biological compounds. Microb Cell Fact 13(1):181.

(Continued)

*Primary Examiner* — Oluwatosin A Ogunbiyi
(74) *Attorney, Agent, or Firm* — N.V. Nederlandsch Octrooibureau

(57) ABSTRACT

The present invention relates to the fields of medical microbiology and vaccines. In particular the invention relates to a process wherein the spontaneous release of bacterial outer membrane vesicles (OMV) of Gram-negative bacteria is stimulated by application of a dissolved oxygen tension (DOT) that is higher than a physiological DOT. The thus produced OMVs are for use in vaccines. The invention further relates to OMV obtainable by said process, and to a pharmaceutical composition comprising such OMV. The present invention further relates to the use of OMV of the present invention as a medicament in particular for use in a method for eliciting an immune response.

19 Claims, 9 Drawing Sheets

Specification includes a Sequence Listing.

(56) References Cited

OTHER PUBLICATIONS

Bernadac A, Gavioli M, Lazzaroni JC, Raina S, Lloubes R. 1998. *Escherichia coli* tol-pal mutants form outer membrane vesicles. J Bacteriol 180(18):4872-8.

Deatherage BL, Lara JC, Bergsbaken T, Rassoulian Barrett SL, Lara S, Cookson BT. 2009. Biogenesis of bacterial membrane vesicles. Mol Microbiol 72(6):1395-407.

Deeudom M, Koomey M, Moir JW. 2008. Roles of c-type cytochromes in respiration in Neisseria meningitidis. Microbiology 154(Pt 9):2857-64.

Dorward DW, Garon CF. 1990. DNA Is Packaged within Membrane-Derived Vesicles of Gram-Negative but Not Gram-Positive Bacteria. Appl Environ Microbiol 56(6):1960-2.

Ellen AF, Albers SV, Huibers W, Pitcher A, Hobel CF, Schwarz H, Folea M, Schouten S, Boekema EJ, Poolman B and others. 2009. Proteomic analysis of secreted membrane vesicles of archaeal Sulfolobus species reveals the presence of endosome sorting complex components. Extremophiles 13(1):67-79.

Gerritzen MJH, Martens DE, Wijffels RH, Stork M. 2017. High throughput nanoparticle tracking analysis for monitoring outer membrane vesicle production. J Extracell Vesicles 6(1):1333883.

Gorringe AR, Pajon R. 2012. Bexsero: a multicomponent vaccine for prevention of meningococcal disease. Hum Vaccin Immunother 8(2):174-83.

Haurat MF, Elhenawy W, Feldman MF. 2015. Prokaryotic membrane vesicles: new insights on biogenesis and biological roles. Biol Chem 396(2):95-109.

Holst J, Martin D, Arnold R, Huergo CC, Oster P, O'Hallahan J, Rosenqvist E. 2009. Properties and clinical performance of vaccines containing outer membrane vesicles from Neisseria meningitidis. Vaccine 27 Suppl 2:B3-12.

Holten E. 1979. Serotypes of Neisseria meningitidis isolated from patients in Norway during the first six months of 1978. J Clin Microbiol 9(2):186-8.

Imlay JA. 2008. Cellular defenses against superoxide and hydrogen peroxide. Annu Rev Biochem 77:755-76.

Korshunov S, Imlay JA. 2006. Detection and quantification of superoxide formed within the periplasm of *Escherichia coli*. J Bacteriol 188(17):6326-34.

Kulp A, Kuehn MJ. 2010. Biological functions and biogenesis of secreted bacterial outer membrane vesicles. Annu Rev Microbiol 64:163-84.

Lappann M, Danhof S, Guenther F, Olivares-Florez S, Mordhorst IL, Vogel U. 2013a. In vitro resistance mechanisms of Neisseria meningitidis against neutrophil extracellular traps. Mol Microbiol 89(3):433-49.

Lappann M, Otto A, Becher D, Vogel U. 2013b. Comparative proteome analysis of spontaneous outer membrane vesicles and purified outer membranes of Neisseria meningitidis. J Bacteriol 195(19):4425-35.

Li Y, Hopper A, Overton T, Squire DJ, Cole J, Tovell N. 2010. Organization of the electron transfer chain to oxygen in the obligate human pathogen Neisseria gonorrhoeae: roles for cytochromes c4 and c5, but not cytochrome c2, in oxygen reduction. J Bacteriol 192(9):2395-406.

Metz B, Hoonakker M, Uittenbogaard JP, Weyts M, Mommen GP, Meiring HD, Tilstra W, Pennings JL, van der Pol LA, Kuipers B and others. 2017. Proteome Analysis Is a Valuable Tool to Monitor Antigen Expression during Upstream Processing of Whole-Cell Pertussis Vaccines. J Proteome Res 16(2):528-537.

Ng VH, Cox JS, Sousa AO, MacMicking JD, McKinney JD. 2004. Role of KatG catalase-peroxidase in mycobacterial pathogenesis: countering the phagocyte oxidative burst. Mol Microbiol 52(5):1291-302.

Pathirana RD, Kaparakis-Liaskos M. 2016. Bacterial membrane vesicles: Biogenesis, immune regulation and pathogenesis. Cell Microbiol 18(11):1518-1524.

Raeven RH, van der Maas L, Tilstra W, Uittenbogaard JP, Bindels TH, Kuipers B, van der Ark A, Pennings JL, van Riet E, Jiskoot W and others. 2015. Immunoproteomic Profiling of Bordetella pertussis Outer Membrane Vesicle Vaccine Reveals Broad and Balanced Humoral Immunogenicity. J Proteome Res 14(7):2929-42.

Rivera J, Cordero RJ, Nakouzi AS, Frases S, Nicola A, Casadevall A. 2010. Bacillus anthracis produces membrane-derived vesicles containing biologically active toxins. Proc Natl Acad Sci U S A 107(44):19002-7.

Roier S, Zingl FG, Cakar F, Durakovic S, Kohl P, Eichmann TO, Klug L, Gadermaier B, Weinzerl K, Prassl R and others. 2016. A novel mechanism for the biogenesis of outer membrane vesicles in Gram-negative bacteria. Nat Commun 7:10515.

Schwechheimer C, Sullivan CJ, Kuehn MJ. 2013. Envelope control of outer membrane vesicle production in Gram-negative bacteria. Biochemistry 52(18):3031-40.

Seib KL, Tseng HJ, McEwan AG, Apicella MA, Jennings MP. 2004. Defenses against oxidative stress in Neisseria gonorrhoeae and Neisseria meningitidis: distinctive systems for different lifestyles. J Infect Dis 190(1):136-47.

Seib KL, Wu HJ, Kidd SP, Apicella MA, Jennings MP, McEwan AG. 2006. Defenses against oxidative stress in Neisseria gonorrhoeae: a system tailored for a challenging environment. Microbiol Mol Biol Rev 70(2):344-61.

Steeghs L, van Vliet SJ, Uronen-Hansson H, van Mourik A, Engering A, Sanchez-Hernandez M, Klein N, Callard R, van Putten JP, van der Ley P and others. 2006. Neisseria meningitidis expressing IgtB lipopolysaccharide targets DC-SIGN and modulates dendritic cell function. Cell Microbiol 8(2):316-25.

Tommassen J, Vermeij P, Struyve M, Benz R, Poolman JT. 1990. Isolation of Neisseria meningitidis mutants deficient in class 1 (porA) and class 3 (porB) outer membrane proteins. Infect Immun 58(5):1355-9.

Tseng HJ, Srikhanta Y, McEwan AG, Jennings MP. 2001. Accumulation of manganese in Neisseria gonorrhoeae correlates with resistance to oxidative killing by superoxide anion and is independent of superoxide dismutase activity. Mol Microbiol 40(5):1175-86.

Van de Waterbeemd B, Mommen GP, Pennings JL, Eppink MH, Wijffels RH, van der Pol LA, de Jong AP. 2013a. Quantitative proteomics reveals distinct differences in the protein content of outer membrane vesicle vaccines. J Proteome Res 12(4):1898-908.

Van de Waterbeemd B, Streefland M, van der Ley P, Zomer B, van Dijken H, Martens D, Wijffels R, van der Pol L. 2010. Improved OMV vaccine against Neisseria meningitidis using genetically engineered strains and a detergent-free purification process. Vaccine 28(30):4810-6.

Van der Ley P, Steeghs L, Hamstra HJ, ten Hove J, Zomer B, van Alphen L. 2001. Modification of lipid A biosynthesis in Neisseria meningitidis IpxL mutants: influence on lipopolysaccharide structure, toxicity, and adjuvant activity. Infect Immun 69(10):5981-90.

Van Deuren M, van der Ven-Jongekrijg J, Bartelink AK, van Dalen R, Sauerwein RW, van der Meer JW. 1995. Correlation between proinflammatory cytokines and antiinflammatory mediators and the severity of disease in meningococcal infections. J Infect Dis 172(2):433-9.

Zollinger WD, Mandrell RE, Griffiss JM, Altieri P, Berman S. 1979. Complex of meningococcal group B polysaccharide and type 2 outer membrane protein immunogenic in man. J Clin Invest 63(5):836-48.

Brandtzaeg P, Kierulf P, Gaustad P, Skulberg A, Bruun JN, Halvorsen S, Sorensen E. 1989. Plasma endotoxin as a predictor of multiple organ failure and death in systemic meningococcal disease. J Infect Dis 159(2):195-204.

Claassen I, Meylis J, van der Ley P, Peeters C, Brons H, Robert J, Borsboom D, van der Ark A, van Straaten I, Roholl P and others. 1996. Production, characterization and control of a Neisseria meningitidis hexavalent class 1 outer membrane protein containing vesicle vaccine. Vaccine 14(10):1001-8.

Espesset D, Corda Y, Cunningham K, Benedetti H, Lloubès R, Lazdunski C, Géli V. 1994. The colicin A pore-forming domain fused to mitochondrial intermembrane space sorting signals can be functionally inserted into the *Escherichia coli* plasma membrane by a mechanism that bypasses the Tol proteins. Molecular Microbiology 13(6):1121-1131.

(56) References Cited

OTHER PUBLICATIONS

Haugaard N. 1968. Cellular mechanisms of oxygen toxicity. Physiol Rev 48(2):311-73.

Hewitt CJ, Nebe-Von Caron G, Axelsson B, McFarlane CM, Nienow AW. 2000. Studies related to the scale-up of high-cell-density *E. coli* fed-batch fermentations using multiparameter flow cytometry: effect of a changing microenvironment with respect to glucose and dissolved oxygen concentration. Biotechnol Bioeng 70(4):381-90.

Malloy A, Carr B. 2006. NanoParticle Tracking Analysis—The Halo™ System. Particle & Particle Systems Characterization 23(2):197-204.

Fredriksen, J. Holst, et al. "Production, characterization and control of MenB-vaccine" Folkehelsa": an outer membrane vesicle vaccine against group B meningococcal disease." NIPH annals 14.2 (1991): 67-79.

Storz, Gisela, and James A. Imlayt. "Oxidative stress." Current opinion in microbiology 2.2 (1999): 188-194.

Thalen, Marcel, et al. "Rational medium design for Bordetella pertussis: basic metabolism." Journal of biotechnology 75.2-3 (1999): 147-159.

Knapp, Joan S. "Historical perspectives and identification of Neisseria and related species" Clinical microbiology reviews 1.4 (1988): 415-431.

Moslen MT. 1994. Reactive oxygen species in normal physiology, cell injury and phagocytosis. Adv Exp Med Biol 366:17-27.

Port JL, DeVoe IW, Archibald FS. 1984. Sulphur acquisition by Neisseria meningitidis. Can J Microbiol 30(12):1453-7.

Paalme T, Kahru A, Elken R, Vanatalu K, Tiisma K, Raivo V. 1995. The computer-controlled continuous culture of *Escherichia coli* with smooth change of dilution rate (A-stat). Journal of Microbiological Methods 24(2):145-153.

Su FH, Tabañag IDF, Wu CY, Tsai SL. 2017. Decorating outer membrane vesicles with organophosphorus hydrolase and cellulose binding domain for organophosphate pesticide degradation. Chemical Engineering Journal 308:1-7.

Zariri A, van der Ley P. 2015. Biosynthetically engineered lipopolysaccharide as vaccine adjuvant. Expert Rev Vaccines 14(6):861-76.

\* cited by examiner

Fig. 1B

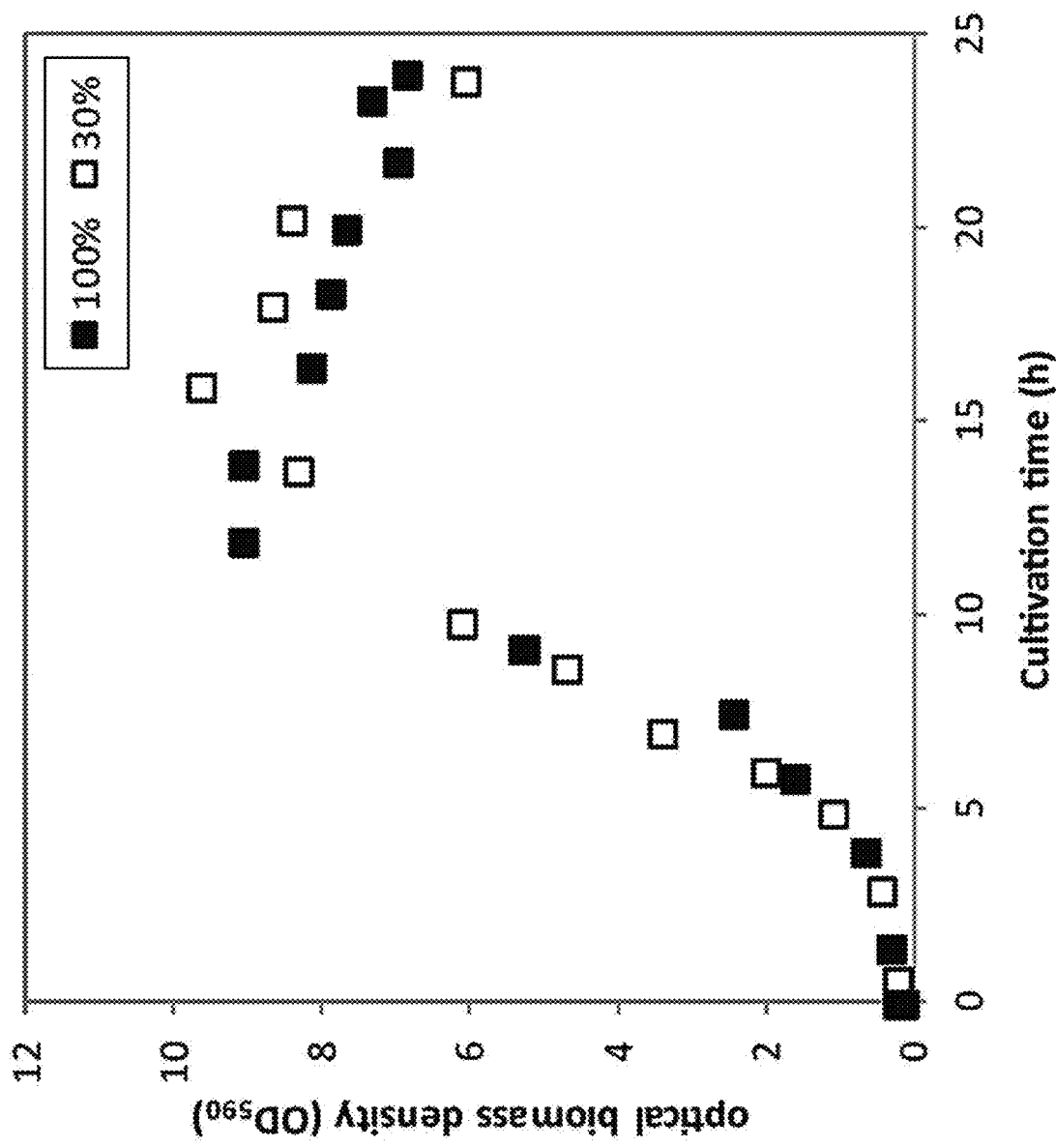

SEQUENCE LISTING

<160> NUMBER OF SEQ ID NOS: 2

<210> SEQ ID NO 1
<211> LENGTH: 299
<212> TYPE: PRT
<213> ORGANISM: Neisseria meningitidis

<400> SEQUENCE: 1

Met Pro Ser Glu Lys Lys Met Cys Ile Glu Met Lys Phe Ile Phe Phe
1               5                   10                  15

Val Leu Tyr Val Leu Gln Phe Leu Pro Phe Ala Leu Leu His Lys Ile
            20                  25                  30

Ala Asp Leu Thr Gly Leu Leu Ala Tyr Leu Leu Val Lys Pro Arg Arg
        35                  40                  45

Arg Ile Gly Glu Ile Asn Leu Ala Lys Cys Phe Ser Glu Trp Ser Glu
    50                  55                  60

Glu Lys Arg Lys Thr Val Leu Lys Gln His Phe Lys His Met Ala Lys
65                  70                  75                  80

Leu Met Leu Glu Tyr Gly Leu Tyr Trp Tyr Ala Pro Ala Gly Arg Leu
                85                  90                  95

Lys Ser Leu Val Arg Tyr Arg Asn Lys His Tyr Leu Asp Asp Ala Leu
            100                 105                 110

Ala Ala Gly Glu Lys Val Ile Ile Leu Tyr Pro His Phe Thr Ala Phe
        115                 120                 125

Glu Met Ala Val Tyr Ala Leu Asn Gln Asp Ile Pro Leu Ile Ser Met
    130                 135                 140

Tyr Ser His Gln Lys Asn Lys Ile Leu Asp Glu Gln Ile Leu Lys Gly
145                 150                 155                 160

Arg Asn Arg Tyr His Asn Val Phe Leu Ile Gly Arg Thr Glu Gly Leu
                165                 170                 175

Arg Ala Leu Val Lys Gln Phe Arg Lys Ser Ser Ala Pro Phe Leu Tyr
            180                 185                 190

Leu Pro Asp Gln Asp Phe Gly Arg Asn Asp Ser Val Phe Val Asp Phe
        195                 200                 205

Phe Gly Ile Gln Thr Ala Thr Ile Thr Gly Leu Ser Arg Ile Ala Ala
    210                 215                 220

Leu Ala Asn Ala Lys Val Ile Pro Ala Ile Pro Val Arg Glu Ala Asp
225                 230                 235                 240

Asn Thr Val Thr Leu His Phe Tyr Pro Ala Trp Lys Ser Phe Pro Gly
                245                 250                 255

Glu Asp Ala Lys Ala Asp Ala Gln Arg Met Asn Arg Phe Ile Glu Asp
            260                 265                 270

Arg Val Arg Glu His Pro Glu Gln Tyr Phe Trp Leu His Lys Arg Phe
        275                 280                 285

Lys Thr Arg Pro Glu Gly Ser Pro Asp Phe Tyr
    290                 295

<210> SEQ ID NO 2
<211> LENGTH: 242
<212> TYPE: PRT
<213> ORGANISM: Neisseria meningitidis

<400> SEQUENCE: 2

Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val

-continued

```
                20                  25                  30
Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
50                      55                  60

Asp Ala Val Ala Ala Pro Glu Pro Glu Pro Glu Pro Glu Pro Ala Pro
65                  70                  75                  80

Ala Pro Val Val Val Val Glu Gln Ala Pro Gln Tyr Val Asp Glu Thr
                85                  90                  95

Ile Ser Leu Ser Ala Lys Thr Leu Phe Gly Phe Asp Lys Asp Ser Leu
            100                 105                 110

Arg Ala Glu Ala Gln Asp Asn Leu Lys Val Leu Ala Gln Arg Leu Ser
        115                 120                 125

Arg Thr Asn Val Gln Ser Val Arg Val Glu Gly His Thr Asp Phe Met
        130                 135                 140

Gly Ser Asp Lys Tyr Asn Gln Ala Leu Ser Glu Arg Arg Ala Tyr Val
145                 150                 155                 160

Val Ala Asn Asn Leu Val Ser Asn Gly Val Pro Val Ser Arg Ile Ser
                165                 170                 175

Ala Val Gly Leu Gly Glu Ser Gln Ala Gln Met Thr Gln Val Cys Glu
            180                 185                 190

Ala Glu Val Ala Lys Leu Gly Ala Lys Val Ser Lys Ala Lys Lys Arg
        195                 200                 205

Glu Ala Leu Ile Ala Cys Ile Glu Pro Asp Arg Arg Val Asp Val Lys
        210                 215                 220

Ile Arg Ser Ile Val Thr Arg Gln Val Val Pro Ala His Asn His His
225                 230                 235                 240

Gln His
```

PROCESS FOR PRODUCING OUTER MEMBRANE VESICLES

FIELD OF THE INVENTION

The present invention relates to the fields of medical microbiology and vaccines. In particular the invention relates to a process for producing spontaneous outer membrane vesicles (OMVs) of Gram-negative bacteria for use in vaccines, to OMVs obtainable by said process, and to a pharmaceutical composition comprising such OMVs. The present invention further relates to the use of OMVs of the present invention as a medicament in particular for use in a method for eliciting an immune response.

SEQUENCE LISTING

The contents of the electronic sequence listing (P6069376PCTUS_SequenceListing.text; Size: 5116 bytes; and Date of Creation: Jun. 2, 2020) is herein incorporated by reference in its entirety.

BACKGROUND ART

Outer membrane vesicles (OMVs) are naturally produced by Gram-negative bacteria and play a role in pathogenesis, cell-to-cell communication and stress responses (Kulp and Kuehn 2010). Membrane vesicle formation has been shown recently in Gram-positive bacteria and archaea as well (Ellen et al. 2009; Rivera et al. 2010). OMVs are spherical nanoparticles and the vesicle consist of a phospholipid bilayer with proteins and lipopolysaccharide (LPS) and the lumen of the vesicle contains periplasmic components of the bacterium (Kulp and Kuehn 2010; Schwechheimer and Kuehn 2015).

Since the OMVs are highly similar to the outer membrane of the bacteria, non-replicating, and characteristically full of pathogen associated molecular patterns, these vesicles have been used successfully as vaccine (Gorringe and Pajon 2012; Holst et al. 2009). These vaccines have been produced by extraction of vesicles from the bacterial outer membrane. In this way, the LPS could be detoxified and vesicles are artificially formed (Fredriksen et al. 1991; Zollinger et al. 1979). However, extraction of vesicles is disadvantageous since differences in the proteome of extracted OMVs (eOMV) and spontaneous OMVs (sOMVs) were found (Lappann et al. 2013; van de Waterbeemd et al. 2013a). Furthermore, extraction methods are not required anymore for detoxification since the possibility of molecular detoxification (van der Ley et al. 2001), which is the basis for the use of spontaneous released OMVs. The use of spontaneous released vesicles simplifies the purification of OMVs since it obsoletes the extraction step in the down-stream processing of the vaccine product (Lappann et al. 2013; van de Waterbeemd et al. 2013a).

Feasible sOMV production has not been straightforward. Despite the research on OMVs over the past 4 decades, the exact mechanism triggering the release of OMVs by a bacterium remains unknown. Because the composition of OMVs differs from the outer membrane of the bacteria, it is generally thought that the release of vesicles is not a stochastic process (Schwechheimer et al. 2013). Biogenesis of OMVs has been described by several models although it remains unclear whether a shared mechanism exists. OMV biogenesis is hypothesized to be based on small peptidoglycan accumulation in the periplasm, less anchoring of the outer membrane to the peptidoglycan layer, or O-antigen charge repulsion. These models are reviewed in (Haurat et al. 2015) and (Schwechheimer and Kuehn 2015). sOMV production by *Neisseria meningitidis* can be increased by deleting the rmpM gene that anchors the outer membrane to the peptidoglycan layer (van de Waterbeemd et al. 2010). Reducing the linkage between the outer membrane and the peptidoglycan layer has been used to improve the sOMV production of *E. coli* (Bernadac et al., J Bacteriol. 1998,180 (18):4872-8).

Recent work by Van de Waterbeemd et al. (2013b) showed that cysteine depletion triggers OMV release by *N. meningitidis*. Van de Waterbeemd et al. showed that the cysteine depletion-triggered release of OMVs is probably mediated through oxidative stress that is caused by cysteine depletion. Indeed, oxidative stress induced by additions peroxide pulses to the medium had a similar but transient effect since sOMVs are released temporarily after each peroxide addition. The addition of hydrogen peroxide, however, is not feasible for scalable OMV production processes since hydrogen peroxide addition to a bacterial culture will result in significant cell death and lysis of bacteria.

There is therefore still a need for more efficient and scalable processes for producing sOMVs.

SUMMARY OF THE INVENTION

In a first aspect, the invention relates to a process for producing spontaneously released bacterial outer membrane vesicles (OMVs), wherein the process comprises the steps of: a) cultivating a population of a Gram-negative bacterium, which cultivation comprises stimulation of the release of OMVs by application of a dissolved oxygen tension (DOT) that is higher than a physiological DOT of 30% air saturation measured at 35° C.; and, b) recovering the OMV released in a), wherein the recovery at least comprises removal of the bacteria from the OMVs. Preferably, in the process the DOT applied to stimulate the release of OMVs is at least 31, 32, 35, 40, 50, 55, 60, 70, 80, 90, 100, 125, 150 or 200% air saturation measured at 35° C., and wherein preferably, the DOT applied to stimulate the release of OMVs is less than 350, 325, 300, 275, 250, 225, 205 or 185% air saturation measured at 35° C.

A process of the invention preferably is a process wherein cultivating the Gram-negative bacterium comprises a mode that employs adding a feeding medium, wherein said mode is selected from fed-batch mode, semi-continuous mode, and continuous mode. More preferably, the process comprises: a) a first phase wherein biomass of the Gram-negative bacterium is accumulated at a first DOT; and, b) a second phase wherein release of OMVs from the biomass accumulated in a) is stimulated by the application of a second DOT that is higher than the first DOT; wherein preferably, the first DOT is a physiological DOT, preferably a DOT of less than 50, 40, 35 or 32% air saturation measured at 35° C.

In the processes of the invention, the Gram-negative bacterium preferably has at least one of: a) a genetic modification which causes the bacterium to produce an LPS with reduced toxicity but which LPS retains at least part of its adjuvant activity; preferably said genetic modification is a modification that decreases or knocks-out expression of one or more genes selected from the lpxL1 and lpxL2 genes or homologues thereof and the lpxK gene or a homologue thereof and/or is a modification that effects the expression of one or more lpxE and/or pagL genes; b) a genetic modification which causes the bacterium to overproduce OMVs as compared to a corresponding wild-type bacterium without the genetic modification, wherein the genetic modification is a modification that attenuates the peptidoglycan-binding activity of one or more proteins comprising a peptidoglycan-associated site, preferably said genetic modification is a modification that decreases or knocks-out expression of one or more genes selected from the group consisting of the tolQ, tolR, tolA, tolB, tolRA, rmpM and ompA genes; and, c) a genetic modification that decreases or knocks-out expression of a gene product, preferably, a gene product selected from the group consisting of cps, a lipid A biosynthesis gene product, PorA, PorB and OpA. The Gram-negative bacterium preferably belongs to a genus selected from the group consisting of the genera *Neisseria, Bordetella, Helicobacter, Salmonella, Vibrio, Shigella, Haemophilus, Pseudomonas, Escherichia, Moraxella, Klebsiella* and *Acinetobacter* preferably the bacterium is of a species selected from the group consisting of *Neisseria meningitidis, Neisseria lactamica, Neisseria gonorrhoeae, Helicobacter pylori, Salmonella typhi, Salmonella typhimurium, Vibrio cholerae, Shigella* spp., *Haemophilus influenzae, Bordetella pertussis, Pseudomonas aeruginosa, Escherischia coli, Moraxella catarrhalis, Klebsiella pneumoniae* and *Acinetobacter baumannii*. In one embodiment, the Gram-negative bacterium expresses an antigen foreign to said Gram-negative bacterium. In another embodiment, the Gram-negative bacterium expresses multiple antigens, wherein preferably the different antigens are chosen such that the major antigen variants are included to improve vaccine coverage.

Preferably, in a process according to the invention the OMVs are sterilized, preferably by filter sterilization, preferably using a filter with pores of less than about 0.3 micrometer.

A process according to the invention can further comprise the step of combining the OMVs with a pharmaceutically accepted excipient and optionally an adjuvant.

In a process according to the invention the OMVs are preferably for use in vaccines.

In a second aspect, the invention pertains to OMVs obtainable by the process of the invention.

In a third aspect, the invention pertains to a pharmaceutical composition comprising OMVs according to, or produced in a process of the invention and a pharmaceutically accepted excipient and optionally an adjuvant.

In a fourth aspect, the invention pertains to said OMVs or said pharmaceutical composition for use as a medicament, preferably in the treatment of meningitis.

DESCRIPTION OF THE INVENTION

Surprisingly, we found that a common control parameter of bioreactor cultivations can be used directly and reliably to trigger the release of spontaneous outer membrane vesicles (OMV).

In a first aspect, the invention relates to a process for producing spontaneously released bacterial outer membrane vesicles. Preferably, the process comprises the step of: a) cultivating a population of a Gram-negative bacterium, which cultivation comprises stimulation of the release of OMV by application of a dissolved oxygen tension (DOT) that is higher than a physiological DOT of 30%. The method further preferably comprises the step of: b) recovering the OMV released in a), wherein preferably, the recovery at least comprises removal of the bacteria from the OMV.

As used herein the term OMVs for "Outer Membrane Vesicles" denotes released spheres of outer membrane with periplasmic content that contain biologically active molecules (toxins, proteins, DNA) produced from the outer membrane of Gram-negative bacteria. OMVs are sometimes also referred to as "blebs". These vesicles are often involved in pathogenic processes since they contribute to the long-distance delivery of bacterial virulence factors, promote inflammation and stimulate host immune response. OMVs formed by bacteria can also mediate intercellular exchange events including cell-cell signalling, protein and DNA exchange (see for example Berleman J et al., 2013).

Cultivation of a population of a Gram-negative bacterium in a process according to the invention may be performed by any method known to the person skilled in the art. A preferred medium for cultivation is a chemically defined medium, e.g. such as described in Baart et al., 2003. The temperature may be varied at any temperature such as between about 30° C. and about 40° C. The pH may be varied at any pH such as at a pH from about 5.5 to about 8.5. Preferred culture conditions comprise culturing at about 35° C. at pH 7.2.

A population of a bacterium is herein defined as at least two bacteria, preferably of the same genus and species.

The method of the invention comprises the application of an increased DOT to stimulate the release of OMVs. The DOT that is applied to stimulate the release of OMVs preferably is a DOT that induces (extracellular) oxidative stress in the bacterium, as may be determined by proteomic profiling of the bacteria. Preferably, the DOT that is applied to stimulate the release of OMV is higher than a physiological DOT for the bacterium, which usually is a DOT of around 30%. Dissolved oxygen tension is herein expressed as percentage of air saturation when measured at 35° C. DOT may be measured, and monitored during fermentation, using a DOT (i.e. oxygen) sensor as are known in the art. The DOT parameter is calculated by means of an oxygen electrode and conventional laboratory techniques. Thus, 100% air saturation corresponds to a solution that is saturated with air, whereas 0% corresponds to a solution that has been thoroughly purged with an inert gas such as nitrogen. Calibration is performed under standard atmospheric pressure conditions, and with conventional air comprising approximately 21% oxygen.

During fermentation DOT may be controlled by means known in the art per se, including e.g. stirrer speed, rate of aeration, fraction of oxygen in the air supply and/or pressure. Preferably, in the methods of the invention, the DOT is not increased by (pulsed) additions of hydrogen peroxide. In a preferred process the DOT applied to stimulate the release of OMV is at least 31, 32, 35, 40, 50, 55, 60, 70, 80, 90, 100, 125, 150 or 200%. Preferably the DOT applied to stimulate the release of OMV is less than 350, 325, 300, 275, 250, 225, 205 or 185%. Preferably, in the method of the invention the DOT applied to stimulate the release of OMV is applied for at least 10, 20, 40 or 60 minutes, more preferably for at least 2, 3, 4 or 6 hours.

In a preferred process said cultivating comprises a mode that employs adding a feeding medium, wherein said mode is selected from fed-batch mode, semi-continuous mode, and continuous mode. Preferably, these modes employ a feeding regime wherein the spontaneous release of OMV is optimally exploited.

A batch process is a cultivation mode in which all the nutrients necessary for cultivation of the cells are contained in the initial culture medium, without additional supply of further nutrients during fermentation. In a fed-batch process, after a batch phase, a feeding phase takes place in which one or more nutrients are supplied to the culture by feeding. One purpose of nutrient feeding can be to increase the amount of biomass (so-called "High-cell-density-cultivation process" or "HCDC") in order to increase the yield of released OMVs as well. Although in most cultivation processes the mode of feeding is critical and important, the present invention is not restricted with regard to a certain mode of feeding.

Feeding of nutrients may be done in a continuous or discontinuous mode according to methods known in the art. The feeding mode may be pre-defined (i.e. the feed is added independently from actual process parameters), e.g. linear constant, linear increasing, step-wise increasing or following a mathematical function, e.g. exponential feeding.

A semi-continuous cultivation process in the meaning of the invention is a process which is operated in its first phase as a fed-batch process (i.e. a batch phase followed by a feeding phase). After a certain volume or biomass has been obtained (i.e. usually when the upper limit of fermenter volume is obtained), a significant part of cell broth containing the OMVs is removed from the bioreactor. Subsequently, feeding is initiated again until the biomass or volume of culture broth has again reached a certain value. This method (draining of culture broth and re-filling by feeding) can be proceeded at least once, and theoretically indefinite times.

In a preferred process the feeding medium is fed at a rate resulting in a specific growth rate that is between 1.0 and 0.05 of the maximum specific growth rate of the bacterium ($\mu_{max}$) in the growth medium. For example the growth rate can be 0.9, 0.8, 0.7, 0.6, 0.5, 0.4, 0.3, 0.2, 0.1 or $0.05\mu_{max}$. In one embodiment, the process comprises a phase during which the specific growth rate is no more than 0.9, 0.8, 0.7, 0.6, 0.5, 0.4, 0.3, 0.2, 0.1 or $0.05\mu_{max}$, whereby preferably the phase during which the specific growth rate is limited to the aforementioned rates is the production phase during which OMVs are released so as to facilitate a high DOT during the production phase. During the production phase there is no need to apply a minimum positive specific growth rate because no growth, or even an observed negative growth rate, during the production phase can be feasible if this results in a higher OMV yield.

In a preferred process of the invention, the process comprises: a) a first phase wherein biomass of the Gram-negative bacterium is accumulated at a first DOT; and, b) a second phase wherein release of OMVs from the biomass accumulated in a) is stimulated by the application of a second DOT that is higher than the first DOT. Preferably, in the first phase the DOT is controlled at a level that supports growth of the bacterium. More preferably, the first DOT applied in the first phase support good or optimal biomass accumulation of the bacterium. The first DOT applied in the first phase therefore preferably is a physiological DOT. Preferably, the first DOT is a DOT of 100% or less, preferably a DOT of less than 75%, 50, 40, 35 or 32% air saturation measured at 35° C. The second phase of the process comprises a stage wherein a second DOT is applied that is higher than the first DOT to stimulate release of OMVs from the biomass accumulated in the first phase. The second DOT can therefore be a DOT applied to stimulate the release of OMVs as described hereinabove. Preferably the second DOT is at least a factor 1.05, 1.1, 1.2, 1.5, 2, 5, or 10 higher than the first DOT.

Preferably, in any of the processes according to the invention the Gram-negative bacterium has a genetic modification which causes the bacterium to produce an LPS with reduced toxicity but which LPS retains at least part of its adjuvant activity; preferably said genetic modification is a modification that decreases or knock-out expression of one or more genes selected from the lpxL1 and lpxL2 genes or homologues thereof and the lpxK gene or a homologue thereof and/or is a modification that effects the expression of one or more lpxE and/or pagL genes. Preferably, the Gram-negative bacterium has at least mutations to decrease or knock-out expression of an lpxL1 gene which encodes an amino acid sequence having at least about 30% sequence identity, more preferably at least about 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 1.

An LPS that is modified to have less toxicity is herein understood as an LPS that is modified to have less toxicity than the toxicity of a corresponding wild-type LPS. Preferably the modified LPS has less than about 90, 80, 60, 40, 20, 10, 5, 2, 1, 0.5 or 0.2% of the toxicity of the corresponding wild-type LPS. The toxicities of wild-type and various modified LPS's with reduced toxicity may be determined in any suitable assay known to the man skilled in the art. A preferred assay for determining the toxicity, i.e. the biological activity of the LPS is the WEHI test for TNF-alpha induction in the MM6 macrophage cell line (Espevik and Niessen, 1986, J. Immunol. Methods 95: 99-105; Ziegler-Heitbrock et al., 1988 Int. J. Cancer 41: 456-461). While it is preferred that the LPS of the Gram-negative bacterium (or its Lipid A moiety) has reduced toxicity, it is further preferred that the LPS retains at least part of its immunostimulatory, i.e. adjuvant activity. Thus, the LPS with reduced toxicity of the Gram-negative bacterium to be used in the invention preferably has at least about 10, 20, 40, 80, 90 or 100% of the immunistimulatory activity of the corresponding wild-type LPS, whereby the immunostimulatory activity is determined by measuring the production of at least one cytokine or the expression of at least one costimulatory molecule upon co-cultivation of dendritic cells (DC).

Heterologous expression of pagL in *N. meningitidis* results in a different attenuated penta-acylated LPS structure, which is still capable of inducing TLR4 activation and induces a TRIF-biased cytokine production on a human monocytic cell line (Pupo et al., 2014, J. Biol. Chem. 289:8668-8680).

Preferably, in any of the processes according to the invention the Gram-negative bacterium has a genetic modification which causes the bacterium to overproduce OMVs as compared to a corresponding wild-type bacterium without the genetic modification, wherein the genetic modification is a modification that attenuates the peptidoglycan-binding activity of one or more proteins comprising a peptidoglycan-associated site, preferably said genetic modification is a modification that decreases or knocks-out expression of one or more genes selected from the group consisting of the tolQ, tolR, tolA, tolB, tolRA, rmpM and ompA genes. A preferred genetic modification that increases OMV production is a genetic modification that reduces or eliminates expression of a gene encoding an anchor protein between outer membrane and peptidoglycan in order to increase vesicle formation and thereby increase OMV yield. A suitable genetic modification for this purpose e.g. reduces or eliminates expression of an OmpA homologue, which are commonly found in Gram-negative bacteria, e.g. the RmpM protein in *Neisseria* spp. (Steeghs et al., 2002 Cell Microbiol, 4:599-611; van de Waterbeemd et al., 2010 Vaccine, 28:4810-4816). Thus, preferably, the genetically modified bacterium has a genetic modification reduces or eliminates expression of an rmpM gene or a homologue thereof. Preferably, the rpmM gene or homologue thereof encodes an amino acid sequence having at least about 30% sequence identity, more preferably at least about 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 2.

Preferably, in any of the processes according to the invention the Gram-negative bacterium belongs to a genus selected from the group consisting of the genera *Neisseria, Bordetella, Helicoibacter, Salmonella, Vibrio, Shigella, Haemophilus, Pseudomonas, Escherichia Moraxella, Klebsiella* and *Acinetobacter*. More preferably, the bacterium is of a species selected from the group consisting of *Neisseria meningitidis, Neisseria lactamica, Neisseria gonorrhoeae, Helicobacter pylori, Salmonella typhi, Salmonella typhimurium, Vibrio cholerae, Shigella* spp., *Haemophilus influenzae, Bordetella pertussis, Pseudomonas aeruginosa, Escherichia coli* and *Moraxella catarrhalis*. Most preferably, the Gram-negative bacterium is a *Neisseria meningitidis* strain that is a replicate or derivative of *N. meningitidis* serogroup B isolate H44/76 (Holten et al., 1979, J Clin Microbiol, 9(2): 186-188; van den Dobbelsteen et al., 2007, Vaccine, 25(13):2491-6).

Preferably, in any of the processes according to the invention the Gram-negative bacterium has one or more mutations to decrease or knock-out expression of a gene product preferably, a gene product selected from the group consisting of cps, porA, porB and opA; many of these mutations are reviewed in WO02/09746.

To decrease or knock-out expression a gene product defined herein, the person skilled in the art has a plethora of well-known tools available. It is routine practice for the person skilled in the art to choose an adequate strategy to introduce a suitable modification in a polynucleotide in order to decrease or knock-out expression of a functional gene product. For example, methods for in vitro mutagenesis are described in Sambrook et al. (Molecular cloning, A laboratory Manual, 2nd ed., Cold Spring Harbor Laboratory Press, Cold Spring Harbor, N.Y., USA, 1989). Corresponding methods are also available commercially in the form of kits (e.g., Quikchange site-directed mutagenesis kit by Stratagene, La Jolla, USA). Deletion of a polynucleotide may, for example, be accomplished by the gene replacement technology that is well known to the skilled person.

Preferably, in any of the processes according to the invention the Gram-negative bacterium expresses multiple PorA subtypes, wherein preferably the population comprises more than one strain of the Gram-negative bacterium, and wherein each strain expresses different PorA subtypes. Preferably, the population of a Gram-negative bacterium comprises multiple species of Gram-negative bacteria such that multiple serotypes of antigen are expressed and finally end up in the OMV preparation. More preferably, a species of Gram-negative bacteria expresses multiple serotypes of an antigen. When the population of bacteria comprises a *N. meningitidis*, the population preferably comprises a *N. meningitidis* expressing multiple serotypes of PorA antigen; more preferably, the population of bacteria comprises multiple species of *N. meningitidis*, each species expressing multiple serotypes of PorA antigen. Preferably, the population of a Gram-negative bacterium comprises three trivalent PorA *N. meningitidis* strains, expressing a total of 9 PorA subtypes (van der Ley et al, 1995, Vaccine, 13(4):401-7; Claassen et al, 1996, Vaccine, 14(10):1001-8; van den Dobbelsteen et al, 2007, supra).

Preferably, in any of the processes according to the invention the Gram-negative bacterium express an antigen foreign to said Gram-negative bacterium. The foreign antigen may be expressed by any means known to the person skilled in the art; preferably the foreign antigen is targeted to the OMV. Preferably, the foreign antigen or a part thereof is fused to or comprised in *N. meningitidis* serogroup B porA or a part thereof, or is fused to the N-terminal part of a surface exposed lipoprotein of a Gram-negative bacterium, such as e.g. described in WO2016/193370. The foreign antigen can be an antigen of a pathogen (infectious agent) and/or of a tumor. For example, the antigen can be from pathogens and infectious agents such as viruses, bacteria, fungi and protozoa.

Within the scope of the invention, it is possible to culture or otherwise provide several different strains of the Gram-negative bacterium, each strain expressing one or more antigens that differ from the antigens expressed in the other strains, e.g. a single or multiple antigen serotypes, and to extract OMVs simultaneously from one or more pooled populations of said bacteria, so as to produce multivalent vaccines. It is also within the scope of the present invention to extract the OMVs separately from different populations of bacteria and then preferably pool the preparations of OMVs. It is further within the scope of the invention that different species Gram-negative bacteria are cultivated together in a single, mixed population or separately in individual populations or even in a combination of individual and mixed populations.

In a process according to the invention, recovery of the OMVs, may be performed by any method known to the person skilled in the art. Preferably, recovery of the OMVs at least comprises removal of the bacteria from the OMVs. A preferred method for removal of bacteria from the OMVs includes one or more filtration steps, optionally including sterile filtration step. Alternatively, bacteria can be removed from the OMVs by centrifugation, optionally followed by sterile filtration of the supernatant.

The OMV preparation obtained by any of the processes according to the present invention can conveniently be stored for future use, either in lyophilized form or in solution, or frozen in solution. In any of the processes according to the present invention, one or several compounds may be added to the OMV preparation such as a (colloidal) stabilizer, such as sucrose, in order to prevent aggregation and/or a preservative such as thiomersal in order to prevent microbial growth.

Preferably, in any of the processes according to the invention the OMVs are sterilized, preferably by filter sterilization, preferably using a filter with pores of less than about 0.3 micrometer. Preferably, sterilization is performed during step b). Filter sterilization also referred to as sterile filtration, is herein defined as filtering a compound of interest through a filter, preferably with pores of between about 0.5 and 0.2 micrometer, such that the filtrate comprising the compound of interest does not comprise any microorganism, or that the amount of microorganism in the filtrate is reduced to an acceptably low level.

After recovery or simultaneously with recovery, the OMV preparation may be purified. Purification may comprise any methods known to the person skilled in the art. Preferably at least one method from the following group is applied: ultrafiltration as described earlier herein and/or diafiltration to exchange the medium, e. g. to remove the metal chelating agent from the extraction medium and/or to concentrate the OMV preparation; degradation of nucleic acids such as deoxyribonucleic acid (DNA) and ribonucleic acid (RNA), which may be performed enzymatically using one or more suitable nucleases, preferably using Benzonase® (Merck, the Netherlands); clarification by filtration, preferably using a filter with a pore size of between about 0.5 µM and 1.0 µM; gel filtration (such as Size Exclusion Chromatography; Sepharose 6 Fast Flow column material; OMVs are recovered from the void volume of the column); sterile filtration as described earlier herein. Preferably, at least sterile filtration is applied. Preferably, more than one purification method is applied. Preferably, the following methods are consecutively applied: ultrafiltration (e.g. 100 or 300 kDa cut-off), diafiltration (e.g. 100 or 300 kDa cut-off), enzymatic degradation of nucleic acids, clarification, gel filtration and sterile filtration, although not necessarily in this order. A preferred process according to the invention does not include ultracentrifugation.

Degradation of nucleic acids using Benzonase® is preferably performed in a buffer of pH 8.4+/−0.4, comprising between about 0.1 to 10 U Benzonase®/ml and between about 1 to 10 mM of $Mg^{2+}$, at 4° C. to 37° C. for 1 to 20 hours.

Preferably, in any of the processes according to the invention the OMV are for use in vaccines. The vaccine may be used for immunization (raising an immune response) or vaccination of a subject, preferably a mammal, preferably a human. In the vaccine, the OMVs may be combined with another antigen to prepare a mixed vaccine, e.g. in combination with vaccines against Neisseria meningitidis serogroup A, C, W135, Y, pneumococcal disease, diphtheria, whooping cough, polio, RSV, tetanus and cholera.

Preferably, in any of the processes according to the invention the volume of the culture in a) and/or the volume of the medium in b) is at least about 10 L, more preferably at least about 1 L, 2 L, 5 L, 10 L, 20 L, 40 L, 60 L 80 L, 100 L, 200 L, 300 L, 400 L, 500 L, 800 L, 1500 L, 5000 L, 10.000 L, 20.000 L or 40.000 L.

Culture may be performed in several steps, including but not limited to a pre-culture or seed-culture and a main culture. The culture can be performed on any scale, including but not limited to shaker flask cultivation, small-scale or large-scale cultivation (including continuous, batch, fed-batch, or solid state cultivation) in laboratory or industrial fermenters.

The present invention further provides a process further comprising the step of combining the OMVs with a pharmaceutically accepted excipient and optionally an adjuvant. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art.

Adjuvants are herein defined to include any substance or compound that, when used in combination with an antigen, to immunize a subject, preferably a mammal, preferably a human, stimulates the immune system, thereby provoking, enhancing or facilitating the immune response against the antigen, preferably without generating a specific immune response to the adjuvant itself. Preferred adjuvants enhance the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animals or humans over a corresponding control group are available in the art. The adjuvant preferably is capable of enhancing the immune response against at least two different antigens.

In a second aspect, the present invention provides OMVs obtainable by any one of the processes according to the first aspect of the present invention. Preferably, said OMV is a product directly obtained or derived from any one of the processes according to the first aspect of the present invention.

The OMV preparation obtainable by any of the processes according to the present invention can conveniently be used for the preparation of a medicament, preferably a medicament for the treatment of meningitis, preferably said medicament is a vaccine against N. meningitidis infection. Preferably, said OMV preparation is a product directly obtained or derived from any one of the processes according to the first aspect of the present invention.

The present invention further provides a pharmaceutical composition comprising OMVs obtainable by any of the processes according to the present invention. In addition to the OMVs, the pharmaceutical composition comprises a pharmaceutically acceptable excipient, such as a carrier, an adjuvant, a stabilizing agent, an osmotic agent, a buffering agent and/or a dispersing agent, e.g. as described earlier herein. Preferably, said pharmaceutical composition is a product directly obtained or derived from any one of the processes according to the present invention.

In a further aspect, the present invention pertains to an OMV obtainable by any of the processes according to the present invention, or to a pharmaceutical composition comprising such OMVs, for use as a medicament. Preferably, the medicament is for use in the treatment of an infectious disease or a tumor. Preferably, said medicament is a vaccine against N. meningitidis infection.

The present invention further provides a method for eliciting in an immune response in a subject, preferably an immune response against a pathogen causing an infectious disease, e.g. N. meningitidis, or against a tumor-associated antigen, the method comprising the step of administering to said subject an effective amount of OMVs obtainable by any of the processes according to the present invention or administering to said subject an effective amount of a pharmaceutical composition comprising said OMVs. Preferably the pharmaceutical composition is a vaccine, preferably a vaccine against N. meningitidis infection.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) Molecular Cloning: A Laboratory Manual, Third Edition, Cold Spring Harbor Laboratory Press, NY; in Volumes 1 and 2 of Ausubel et al. (1994) Current Protocols in Molecular Biology, Current Protocols, USA; and in Volumes I and II of Brown (1998) Molecular Biology LabFax, Second Edition, Academic Press (UK); Oligonucleotide Synthesis (N. Gait editor); Nucleic Acid Hybridization (Hames and Higgins, eds.).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

All patent and literature references cited in the present specification are hereby incorporated by reference in their entirety.

The present invention is further described by the following examples which should not be construed as limiting the scope of the invention.

EXAMPLES

Example 1

Figure 1A:
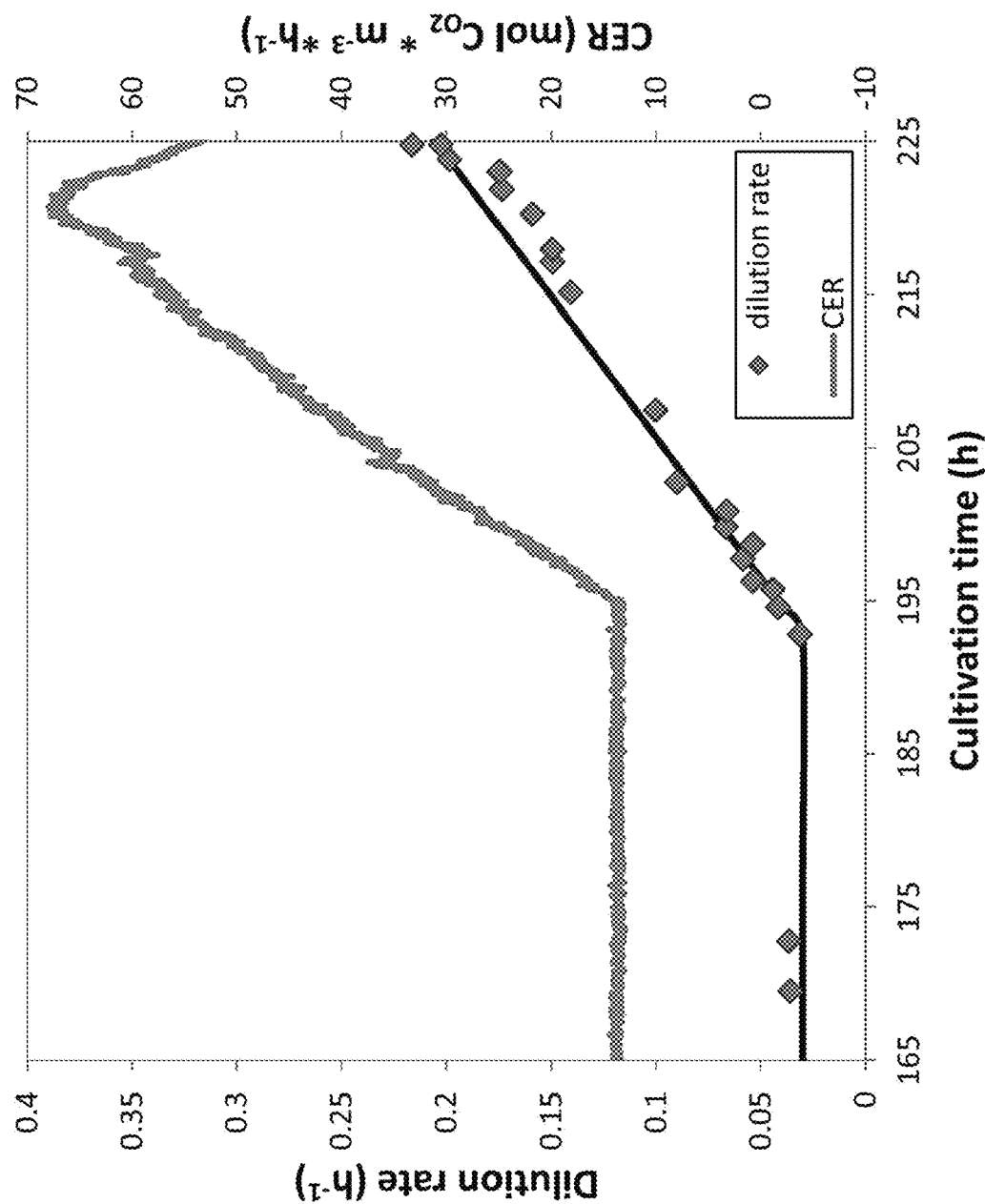
FIG. 1. Accelerostat cultivation of *N. meningitidis*. Graph A shows the increase of the dilution rate (black line, $a_D$ of 0.0055 $h^{-2}$), the actual measured dilution rate (diamonds), and the carbon dioxide evolution rate in time (grey line). Graph B shows the resulting specific sOMV productivity at different dilution rates for the accelerostat (black) and chemostats (grey).

Materials and Methods
Bacterial Strains

A recombinant derivate of the *N. meningitidis* serogroup B isolate H44/76 (Holten 1979) was used in this study. The selected strain was a PorA lacking derivate of the H44/76 isolate. This strain has a non-encapsulated phenotype due to the siaD knockout, lpxL1 deletion to attenuate LPS-toxicity, rmpM deletion to improve vesicle formation (unless indicated otherwise) and IgtB mutation to promote interactions with dendritic cells (Steeghs et al. 2006; van de Waterbeemd et al. 2010). This strain was stored in glycerol as working seedlots. All cultivations were performed in chemically defined growth medium (Baart et al. 2007b). Growth on sulfate was performed after adaptation since cysteine is the preferred sulfur source (Port et al. 1984). Adaptation was performed by sub-culturing the strain in shaker flasks with lower cysteine concentration and subsequent growth in medium without cysteine.

Bioreactor Cultivations

Batch cultivations were performed in 5-liter dished bottom Applikon bioreactors with an H/D ratio of 1.6 based on total volume. Cultivations were operated with 3 liter working volume on a Pierre Guerin Tryton[i] controller. Temperature was controlled at 35±0.5° C. and pH was controlled at pH 7.2±0.05 using 1M HCl and 1M NaOH. Dissolved oxygen tension (DOT) was controlled at 30% unless indicated otherwise. The membrane covered amperometric oxygen sensor (InPro 6850i, Mettler Toledo) was calibrated at 100% in air-saturated sterile culture medium of 35° C. In the first phase of the cultivation, DOT is controlled by increasing the agitation rate (300-1000 RPM) and next the fraction of oxygen is increased in the headspace aeration (1 NL/min) by the addition of pure oxygen. The agitation rate of the 100% DOT cultures was set at 1000 RPM directly after inoculation after which the DOT was controlled by the addition of pure oxygen in the headspace. Samples were taken for optical density measurements and used for nutrient and sOMV measurements after sterile filtration (0.22 μm) and storage at 4° C. Off-gas composition was analyzed by a Thermo Prima δb process mass spectrometer.

Continuous Cultivations

Continuous cultivations were performed in a similar setup as the batch cultivation setup. The working volume of the 5-liter bioreactor was decreased from 3.0 liter to 2.0 liter to reduce the feed medium required for the experiments. The vessel was equipped with a medium inlet and two outlet pipes, one submerged in the cultivation broth at the height of the stirrer and one directly at the liquid-gas interphase. The latter allowed the control of the working volume to be exactly 2.0 liter at a fixed maximum stirrer speed, independent of foaming. The weight of the bioreactor, the feed medium and the pH titrant solutions was measured by balances and used for verification of the dilution rate. Samples were taken for optical density measurements and off-gas analysis was similar to the batch cultivation. The bioreactor was controlled with the same control loops as used in the batch cultivations. After 8 hours of growth the feed and the bleed pumps were started to initiate a continuous culture. Steady state of the culture was assumed based on stable bacterial density values and stable carbon dioxide emission for at least 3 dilutions of the bioreactor volume.

Accelerostat and DOT-Changestat Cultivation

An accelerostat was started from a chemostat fermentation in steady state at D=0.03 $h^{-1}$, operated as described in the previous section, by increasing the dilution rate linearly with $a_D$=0.0055 $h^{-2}$. The dilution rate was changed by increasing the medium inflow rate and equally increasing the broth outflow rate. From the culture broth, 50 mL samples were drawn to purify sOMVs. The sample was centrifuged at 4000×g for 30 min at 4° C. and the sterile filtered supernatant (Nalgene RapidFlow 0.2 μm PES filter unit) was concentrated on 100 kDa spin filters. The concentrated sOMVs were washed with 3% sucrose buffered by TrisHCl (pH 7.4) to wash out contaminating proteins. Next, the diafiltrated sOMVs were centrifuged at 125.000×g for 2 h. The sOMV containing pellet was dissolved in 1 mL TrisHCl pH 7.4 with 3% sucrose.

The DOT-changestat was started from a chemostat culture. For this, a continuous culture in steady state with μ=0.04 $h^{-1}$ was obtained as described previously. During this steady state, the DOT was controlled at 30%, the starting point for the DOT-changestat. From the start of the DOT changestat, the DOT was increased linearly with a DOT=1.0%/h.

Quantification of sOMVs and Metabolites Culture samples were sterile filtered (0.22 µm) before the sOMVs were measured. sOMVs were measured with a phospholipid specific probe FM 4-64 (SynaptoRed C2, Biotium) by mixing 50 µL of diluted samples or OMV with a known concentration with 50 µL of dye solution (0.05 mM FM 4-64). Fluorescence was measured directly after mixing this solution using a plate fluorometer (Synergy MX, Biotek ex480, em650). The concentration of sOMVs in the culture supernatants was calculated from a calibration curve which was based on the responses of the standards (sOMVs corresponding with 0-2.5 mg/L total protein and eOMVs corresponding with 0-10 mg/L total protein). In the DOT-changestat experiments nanoparticle tracking analysis (Malloy and Carr 2006) was used for sOMV quantification. Static measurements (10 captures of 30-seconds) were made on a NanoSight NS500 with 488 nm laser module and sCMOS camera, that was calibrated with the concentration upgrade (MalvernInstruments 2015). Temperature was controlled at 25° C. and captures were analyzed with the NTA 3.2 software build 3.2.16. Automated flow measurements were made as described previously (Gerritzen et al. 2017).

OMV size was assessed by dynamic light scattering in a Zetasizer Nano-ZS with Zetasizer 7.11 software (Malvern Instruments). Measurements were performed using a SOP that takes three measurements in backscatter mode, with auto measurement duration and "seek for optimal position" as positioning setting. The sample was assumed to be protein with a refractive index of 1.450 and 0.001 absorption, in water as dispersant with a viscosity of 0.8872 cP and refractive index of 1.330. Data was processed with the normal analysis model.

Results sOMV Release as a Function of Growth Rate

Figure 1B:
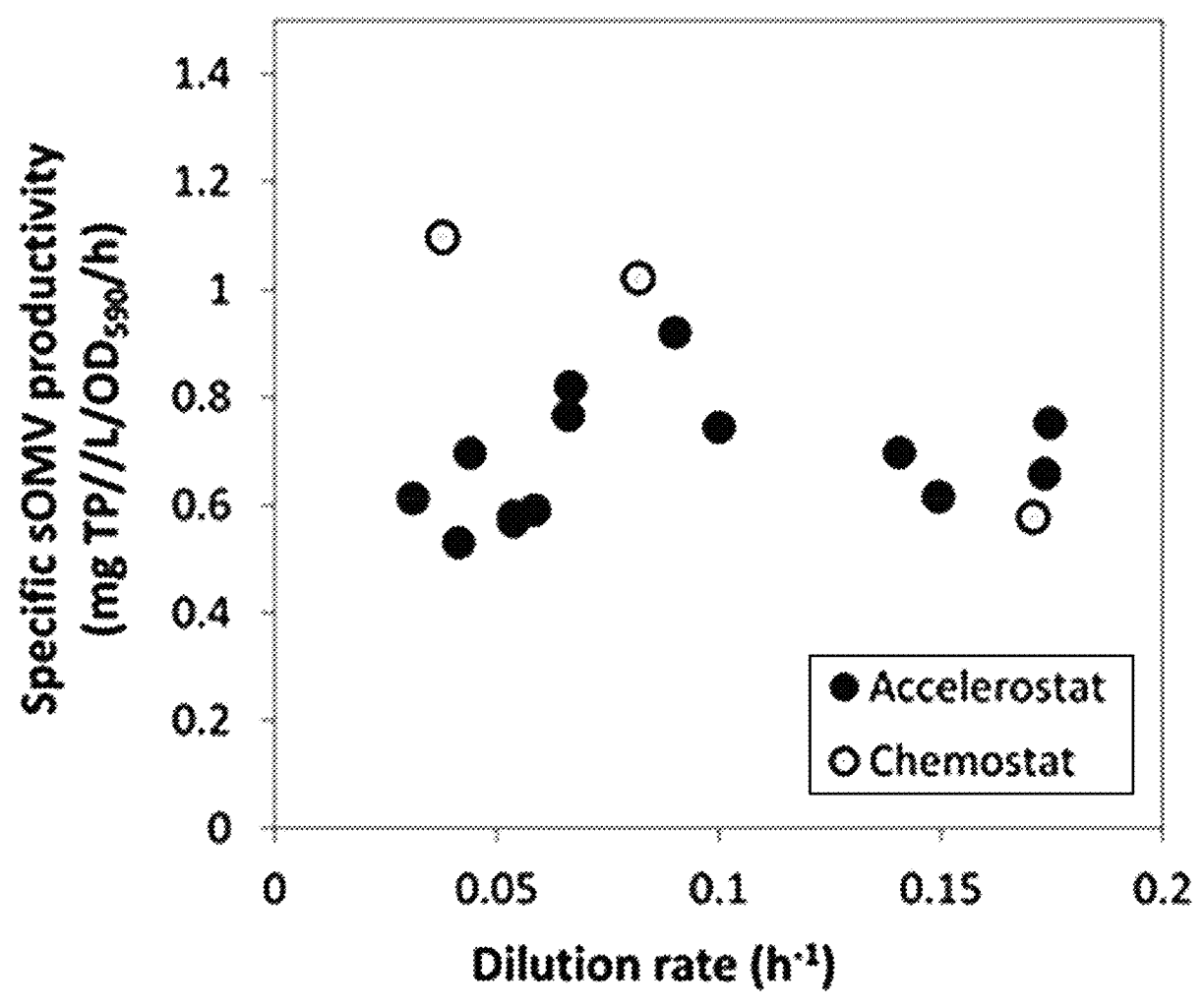

The increased productivity of OMVs during the stationary phase of a batch cultivation (van de Waterbeemd et al. 2013b) raised the question what the direct influence of the growth rate on the OMV release was. Here we assess the influence of growth rate on OMV release in an accelerostat, by slowly increasing the dilution rate of a chemostat culture of *N. meningitidis*. The slow change in dilution rate ($a_D$) should keep the culture in steady state in this accelerostat approach (Paalme et al. 1995). In this accelerostat an $a_D$ of 0.0055 $h^{-2}$ was used (FIG. 1). The carbon dioxide evolution rate (CER) increased simultaneously with the dilution rate up to a dilution rate of 0.18 $h^{-1}$, indicating accordingly increased growth rate. OMVs were produced throughout the accelerostat and these were similar in size and protein composition (data not shown). Altered growth rate from 0.03 $h^{-1}$ to 0.18 $h^{-1}$ showed not to influence the specific sOMV productivity (FIG. 1). Chemostat cultures of *N. meningitidis* at three different growth rates confirmed these results. From these results, we conclude that reducing the growth rate (e.g. from 0.18 $h^{-1}$ to 0.03 $h^{-1}$) is not a trigger for sOMV release.

Influence of Oxidative Stress Assessed by a DOT-Changestat

Figure 2A:
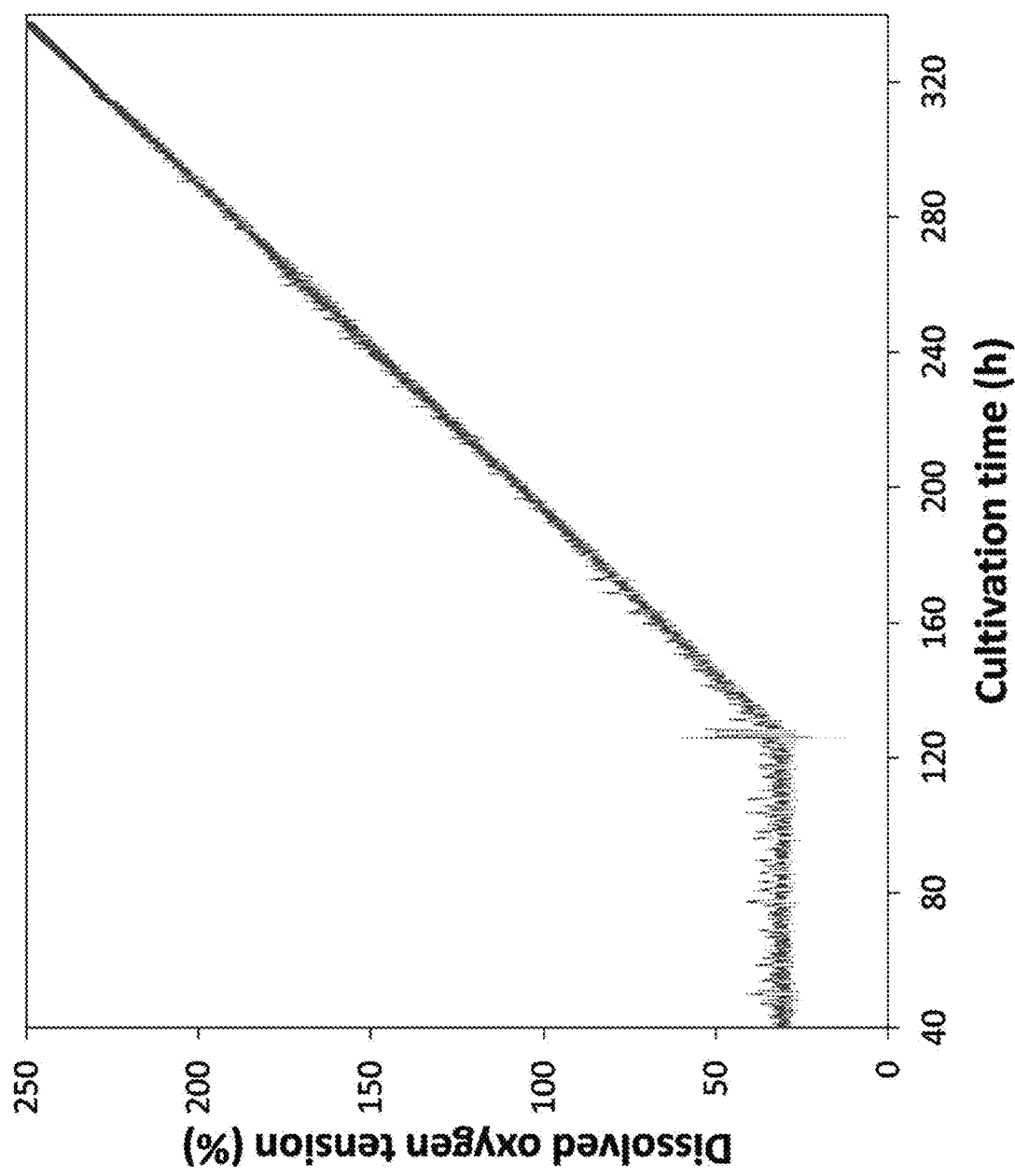
FIG. 2. The influence of increased dissolved oxygen tension on the growth of *N. meningitidis*. Graph A shows the control of the dissolved oxygen in the DOT-changestat, where the DOT setpoint was increased by 1% per hour. The effect of the elevated DOT on the growth is shown in Graph B, whereas both bacteria are capable of handling high levels of DOT. The release of vesicles was found to increase with higher DOT (Graph C).
Figure 2B:
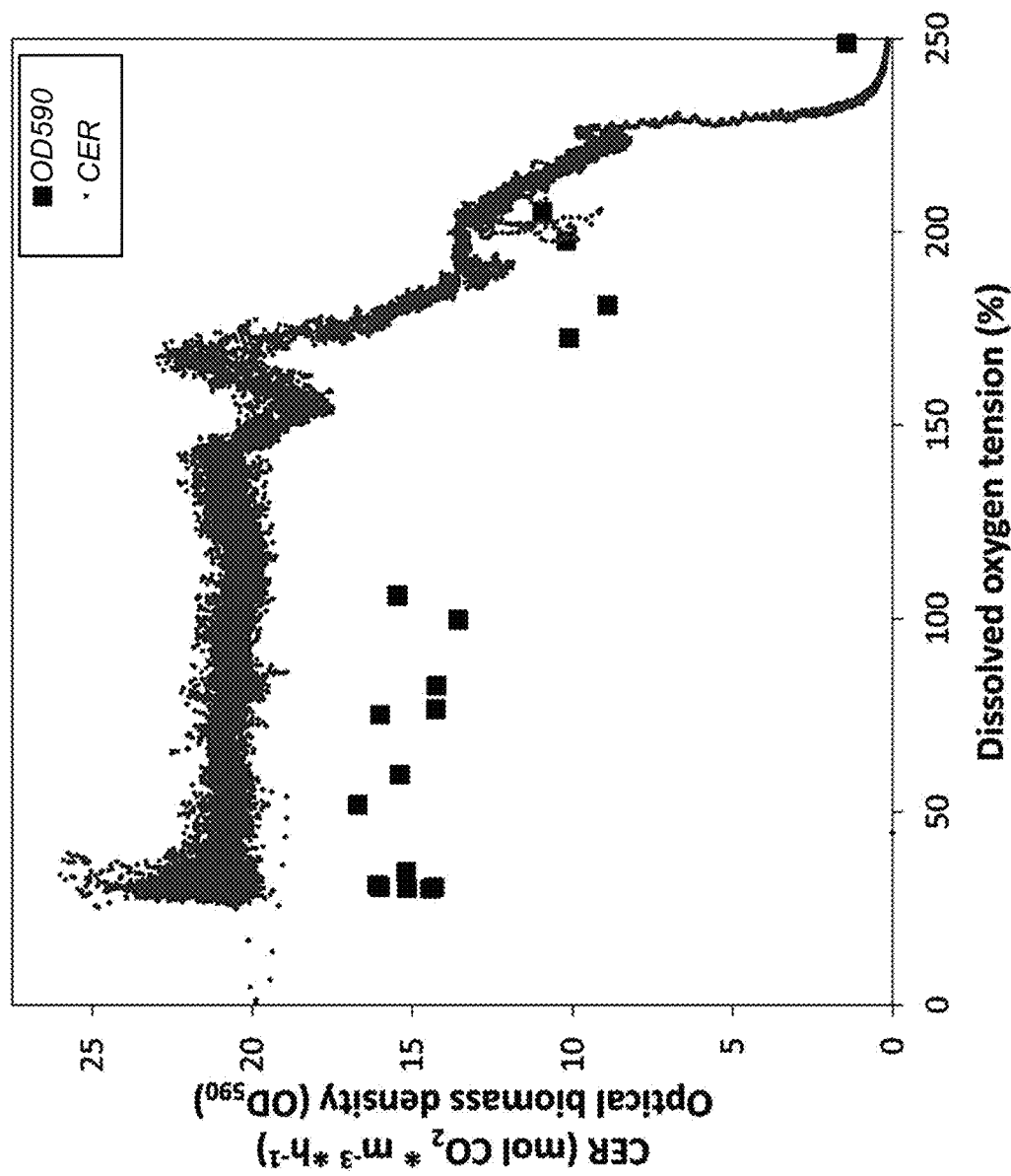
Figure 2C:
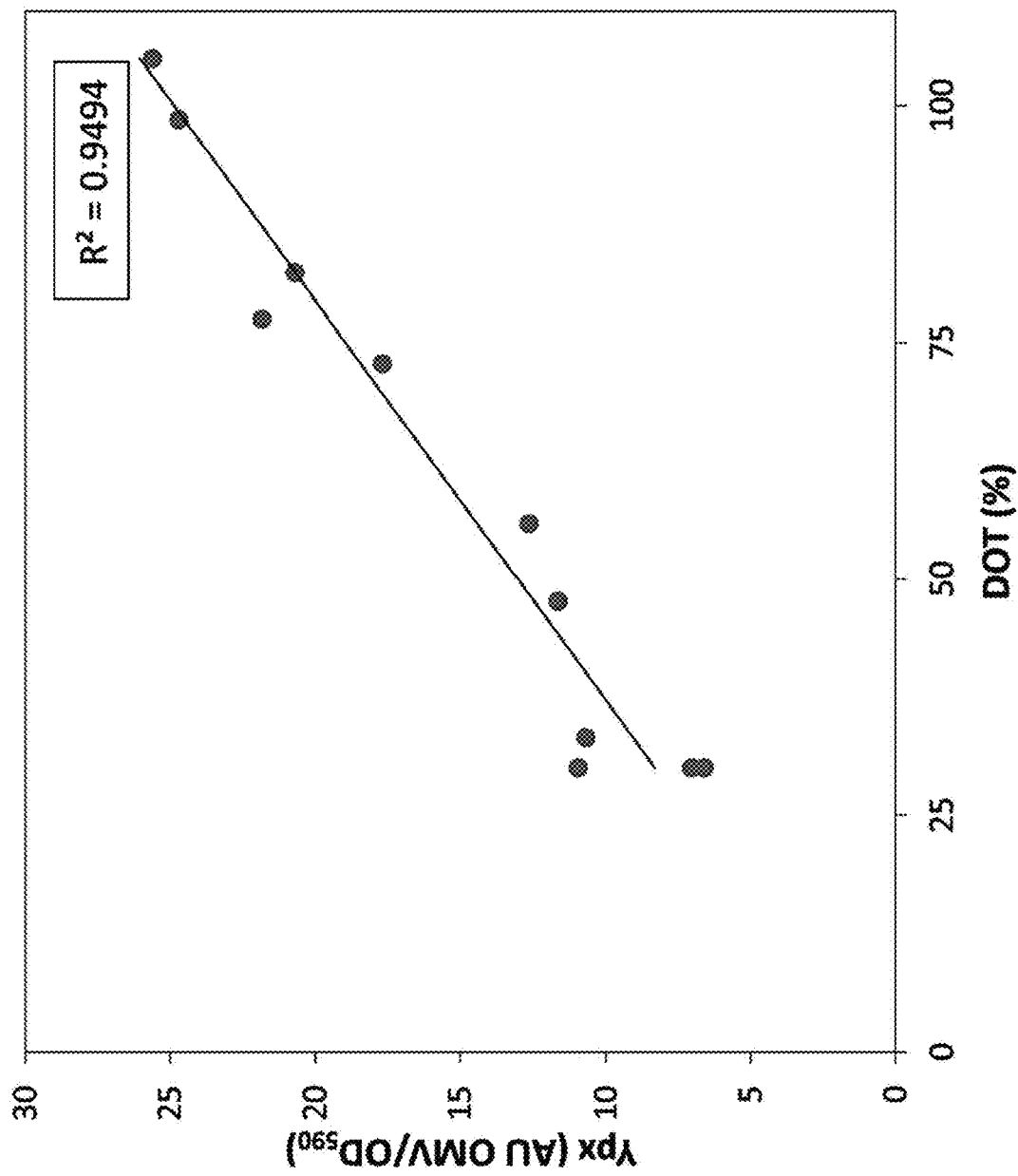
Figure 4A:
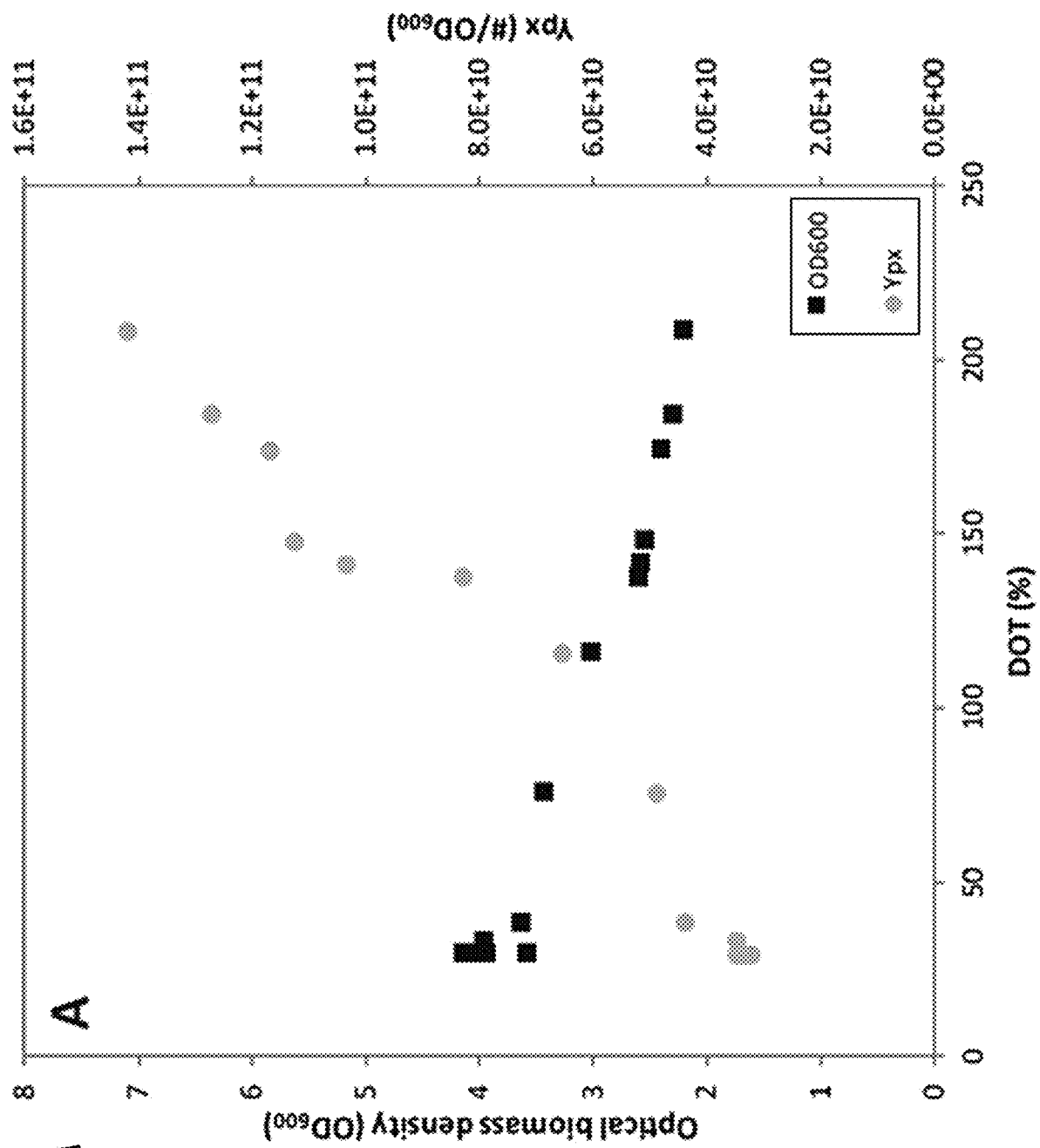
FIG. 4. DOT triggers OMV release in *Escherichia coli* and *Bordetella pertussis*. DOT changestat of *E. coli* (A) shows growth at DOT levels up to 200% in a DOT changestat with $\alpha_{DOT}$=1.5%/h. OMV release is directly related to the increased DOT. *B. pertussis* (B) shows growth up to DOT of 180% in a DOT changestat experiment with $\alpha_{DOT}$=1.0%/h, after which carbon dioxide concentrations in the off-gas showed to decrease.
Figure 4B:
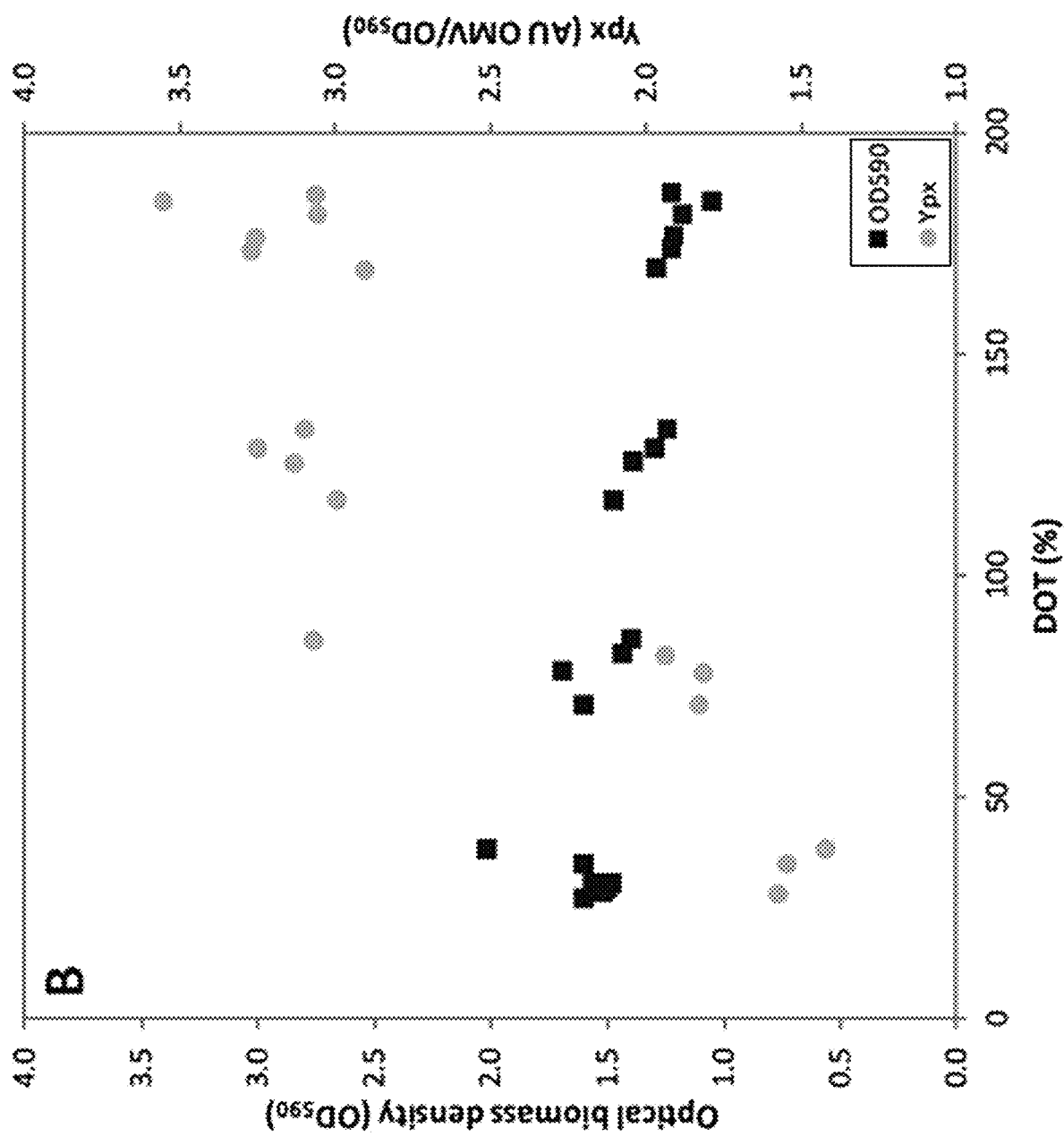

Since reduced growth rate alone was not applicable as trigger of sOMV release, we hypothesized that oxidative stress might be used to directly induce sOMV release. We therefore assessed the effect of oxidative stress on the sOMV release. We have previously shown the release of vesicles under hydrogen peroxide addition (van de Waterbeemd et al. 2013b). This method of hydrogen peroxide addition, however, is not feasible for scalable production processes of OMVs since local hydrogen peroxide addition to a bacterial culture will result in significant cell death and lysis of bacteria. We next tested whether extracellular oxidative stress could be induced by high concentrations of dissolved oxygen, which is one of the controlled parameters in bioreactor cultivations. The DOT is typically kept low, to minimize the stress from hyperoxia and to prevent oxygen inhibition (Haugaard 1968). Especially for a facultative anaerobic pathogen it is standard practice to design the cultivation with low DOT. For example, our *N. meningitidis* cultivation for both the vaccine concepts Hexamen and Nonamen has been designed with DOT levels of 30% air saturation (Baart et al. 2007a; Claassen et al. 1996). Here we assessed the impact of increased DOT on the bacterial growth and the OMV release with a changestat approach. For this DOT-changestat, the DOT of a chemostat culture is linearly increased to maintain a steady state culture (FIG. 2A). *N. meningitidis* shows to be capable of growth up to 150% DOT without significant impact on online measurements (FIG. 2B). Higher levels of DOT result in a rapid reduction of carbon dioxide production and a lower biomass concentration due to wash-out and lysis. Carbon dioxide production is observed up to a DOT of 220%. The release of sOMVs is linearly linked to the concentration of oxygen in the culture broth (FIG. 2C). OMV production can be increased by a factor of 4 by high DOT, while preserving the growth of bacteria. DOT-changestat experiments of *E. coli* and *B. pertussis* in Example 2 showed a similar correlation of increased OMV release at increased DOT levels (FIG. 4). Inducing OMV production at high DOT is thus applicable to Gram-negative bacteria in general.

Improved Productivity of Batch Cultures at Increased Oxygen Concentrations

Figure 3B:
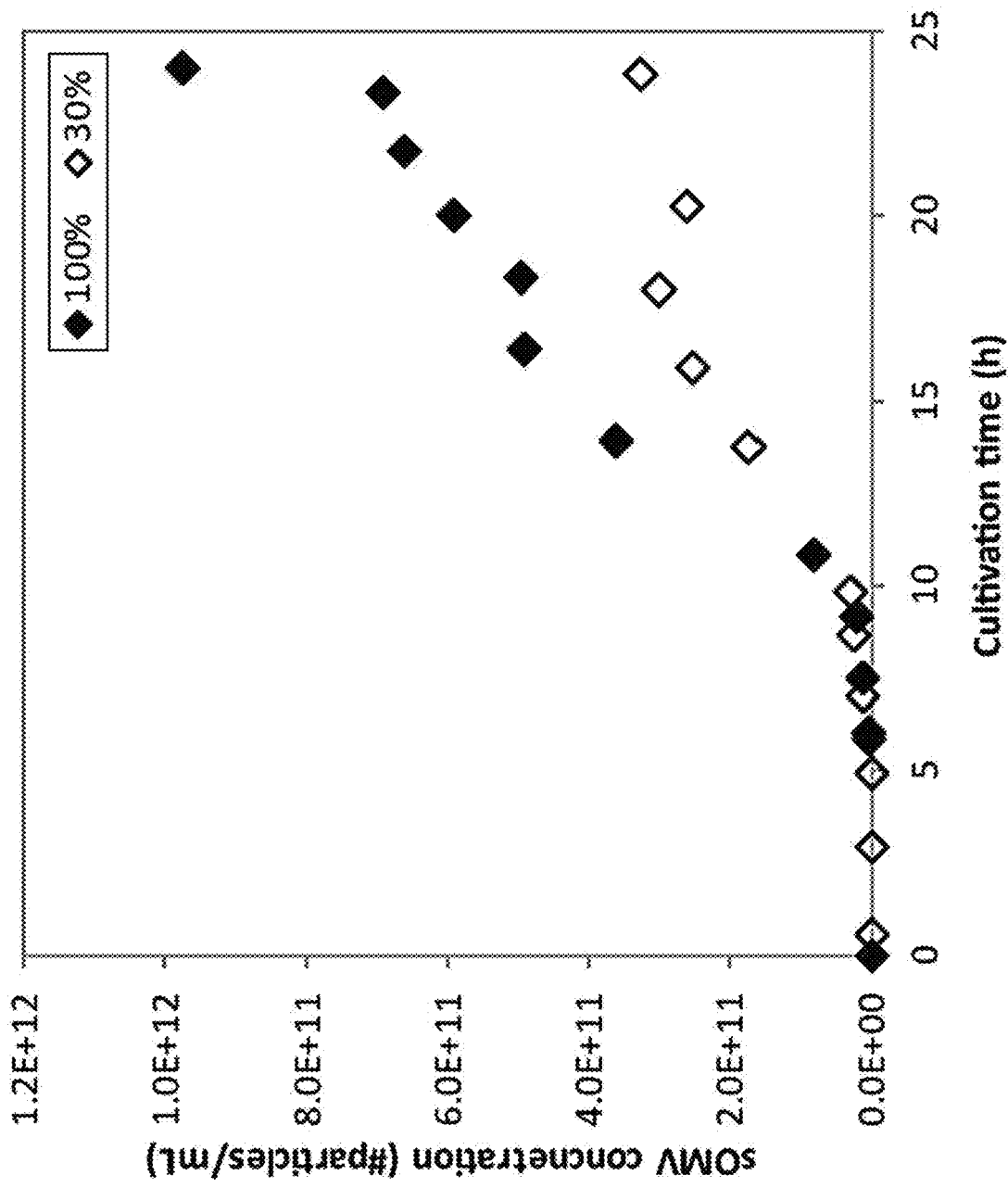
FIG. 3. High dissolved oxygen tension induces OMV release in *N. meningitidis* batch cultures. Growth curves of *N. meningitidis* batch cultures controlled at 30% and 100% air saturation show similar growth (Graph A). The increased oxygen concentration showed to induce a higher level of vesicle release (Graph B). Graphs are the overlay of two replicate cultures to practically allow for sufficient data points covering 24 h. The first replicate consists of data points at 0 h to 12 h cultivation and at 24 h cultivation, and the second replicate at 0 h and 15 h to 22 h.

The high oxygen concentration was then applied to batch cultivation to assess the feasibility of increased sOMV yield in a batch culture. A dissolved oxygen tension of 100% air saturation was used since this value showed increased OMV release while maintaining similar growth characteristics as at 30% air saturation in the changestat (FIG. 2). Bacteria were grown in chemically defined medium that triggers sOMV release from the onset of the stationary phase. The bacterial growth profile was similar for the batch cultures at 30% and 100% air saturation, showing the capability of *N. meningitidis* to deal with higher oxygen concentrations (FIG. 3A). The higher oxygen concentration triggered an increased release of vesicles resulting in a three-times higher productivity at the end of the culture compared to the standard level of 30% (FIG. 3B). The size of OMVs remain constant throughout the culture and is similar between the two concentrations (data not shown). High dissolved oxygen levels also showed to be a potent inducer of sOMV release in batch cultures.

Example 2

Materials and Methods

*Escherichia coli*

*E. coli* JC8031 (TolRA) was used for the DOT-changestat of *E. coli* (Espesset et al. 1994). A shaker flask culture was started by adding 10 µL of frozen glycerol stock (−80° C.) to 100 mL LB medium (Large Capsules: tryptone 10 g/L, yeast extract 5 g/L, NaCl 10 g/L, MP Biomedicals) and incubating the shaker flask at 37° C. for 16 hours. Bioreactor cultivations were performed on LB medium without antifoam with a maximum stirrer speed of 600 RPM at 37° C.

*Bordetella pertussis*

The *B. pertussis* vaccine strain BP509 was used in this study (van Hemert 1967). A chemically defined medium was used without magnesium sulfate (Metz et al. 2017; Thalen et al. 1999). The DOT-changestat was started similarly to the

*N. meningitidis* cultivation described above, with a dilution rate of the DOT-changestat of 0.05 h$^{-1}$. A 7 L Applikon bioreactor with 5.4 L working volume was used with H/D ratio of 2.2 based on total volume.

Results

The release of OMVs by increased DOT levels is not limited to *N. meningitidis* but also extend to other Gram-negative bacteria. We tested the influence of oxidative stress on *B. pertussis* and *E. coli* in DOT-changestat experiments (FIG. 4). Both bacteria showed enhanced vesicle formation under increased DOT. *E. coli* was capable of handling DOT of over 200% after which the experiment was stopped. *B. pertussis* showed a reduction in carbon dioxide evolution rate at DOT of over 180%, after which the cultivation was terminated.

Furthermore, the biomass concentrations of both cultures showed a clear decrease upon higher DOT. This relation was also observed for *N. meningitidis*. We hypothesize that relatively more energy is required for maintenance under oxidative stress. Since the experimental setup was a chemostat with a fixed nutrient supply and dilution rate, the increased energy requirement for maintenance is show as decrease in biomass concentration since less energy is available for bacterial growth.

During the *B. pertussis* DOT changestat, the pH control was affected by blockage of the pH titrants during the experiment at the DOT setpoint of around 80% DOT. This has resulted in a linear increase in pH from 7.2 to 7.4 within 3 hours, followed by a rapid drop in pH to 5.5 due to over addition of acid. After this rapid reduction, the setpoint of pH 7.2 was quickly maintained again by the controller (data not shown). Remarkably, at this time-point a high sOMV concentration was observed, but the exact effects of this deviation are unknown. This deviation did not impact the conclusion on the relation between increased DOT on the vesicle release of *B. pertussis*, since the effect was already observed between 30% and 80% DOT.

Discussion Regarding Examples 1 and 2

In this study we investigated external signals to induce OMV formation. Results show that growth rates from 0.03 $h^{-1}$ to 0.18 $h^{-1}$ do not influence the biogenesis of OMVs. Oxidative stress did trigger OMV release and could be applied directly to bioreactor cultures by increasing the dissolved oxygen tension of these cultures. Oxidative stress could be applied directly to bioreactor cultures by increasing the DOT of these cultures. DOT-changestat cultures show the Gram-negative bacteria to be capable of handling dissolved oxygen concentrations of up to 200% air saturation. Elevated DOT directly increased OMV release. OMV productivity was increased four-fold in a DOT-changestat culture at 120% DOT and three-fold in a batch culture controlled at 100% DOT. Applying increased DOT on *E. coli* and *B. pertussis* results in similar increases in OMV release indicating that this method is broadly applicable to Gram-negative bacteria.

The production of OMVs by oxidative stress could be triggered in the bioreactor by controlling the oxygen concentration in the culture broth. The oxidative stress trigger was observed to trigger OMV release on top of the known mutations on increased OMV formation (Bernadac et al. 1998; Deatherage et al. 2009; van de Waterbeemd et al. 2010). These mutations reduce the linkage between the outer membrane and the peptidoglycan layer. For the *N. meningitidis* DOT-changestat we used a rmpM knockout strain to assess the effect of oxygen on vesicle release, although we also tested the effect of high DOT on a related strain that contained RmpM (data not shown). High DOT levels in a DOT-changestat did trigger increased vesicle release in *N. meningitidis* that contained RmpM too, although the OMV yield per liter culture remained lower than in the rmpM knockout cultures.

Oxidative stress may be a general mechanism to induce OMV release. Here we showed this relation for *N. meningitidis, E. coli* and *B. pertussis*. Sabra et al. showed by electron micrographs that *Pseudomonas aeruginosa* forms more vesicles under extreme oxidative stress ($pO_2$~350% of air saturation) conditions compared to anoxic ($pO_2$~0) conditions (Sabra et al. 2003). Biologically the response of forming OMVs by the bacterium could be explained as a response to avoid phagocytosis by macrophages. During infection, sOMV release probably contribute to disease progression and the severity of fulminant meningococcal sepsis (Brandtzaeg et al. 1989; van Deuren et al. 1995). *N. meningitidis* encounters oxidative stress upon oxidative bursts of phagocytes (Moslen 1994; Ng et al. 2004). Lappann et al. showed that sOMVs of *N. meningitidis* induced the formation of neutrophil extracellular traps (NETs) and binding of OMVs to NETs served as a decoy for the bacteria to circumvent binding to the NETs (Lappann et al. 2013a). The role of OMVs in the interaction with phagocytes should gain more interest.

The growth rate showed to influence the oxidative stress responses. Production of oxidative stress is a characteristic of aerobic bacterial growth as components of the respiratory chain are oxidized (Storz and Imlay 1999). *Neisseria* spp. are oxidase positive pathogens containing a mitochondrial like respiratory chain (Bøvre 1984). *Neisseria* species typically show high levels of respiration (Archibald and Duong 1986). The *N. meningitidis* genome encodes multiple small c-type cytochromes and a single terminal cytochrome oxidase of the cbb3 type (Aspholm et al. 2010; Deeudom et al. 2008; Li et al. 2010; Seib et al. 2006). Li et al. hypothesized that the high respiratory capacity of *Neisseria* spp. and the excess capacity for oxygen reduction acts as defence against endogenous reactive oxygen species (ROS) (Li et al. 2010). SodA and MntC are the major effectors involved in the *Neisseria* spp. oxidative stress response (Seib et al. 2004; Tseng et al. 2001). In the accelerostat experiments in this study, the growth rate increases linearly with the CER up to a growth rate of 0.18 $h^{-1}$. At higher dilution rates, a reduction in CER was observed and the experiment was stopped. The maximum specific growth rate of *N. meningitidis* on this medium is 0.5 $h^{-1}$ (van de Waterbeemd et al. 2010) and wash-out is thus not expected at this dilution rate. The chosen acceleration rate was moderately high ($a_D$=0.0055 $h^{-2}$) and possibly more time for adaptation was required to adapt to the increased growth rates. The chosen acceleration rate possibly resulted in an underestimation of the effect of the higher dilution rates. These chemostats showed depletion of the carbon sources glucose and glutamate and the cultures were likely carbon limited. At lowered growth rates, a lower bacterial density was observed that can be explained by the increased energy requirement for maintenance.

Our initial results show that OMV-size was not affected although oxidative stress can cause damage to bacteria. In general, elevated oxygen concentrations could affect bacterial growth and the production of biological compounds (Baez and Shiloach 2014). *Neisseria* spp. are adapted to ROS production, caused by the respiratory system since reactive oxygen species accumulate as byproducts of the aerobic respiration (Imlay 2008; Korshunov and Imlay 2006), and contain several methods to handle ROS (Seib et al. 2004; Seib et al. 2006). The DOT changestat experiments showed that increased DOT can be controlled such that growth remains possible. Applications, such as the additions of enzymes on OMVs (Alves et al. 2015; Su et al. 2017), could also benefit from this production method.

This disclosure expands the knowledge on sOMV productivity and enhances the process control. We used the dissolved oxygen tension of bacterial cultivations to induce oxidative stress to test the influence of oxidative stress on the vesicle release. Though, it is not obvious to design a fermentation process with a high DOT for a facultative aerobic micro-organism (Hewitt et al. 2000), but it showed to be a convenient process parameter to induce outer membrane vesicle formation. Besides the induced oxidative stress by altering the metabolism, increased DOT may be a more simplistic and better controllable approach. With this approach, it becomes possible to feasibly produce sOMV from Gram-negative cultures for many applications.

REFERENCES

Alves N J, Turner K B, Daniele M A, Oh E, Medintz I L, Walper S A. 2015. Bacterial Nanobioreactors—Directing Enzyme Packaging into Bacterial Outer Membrane Vesicles. ACS Appl Mater Interfaces 7(44):24963-72.

Archibald F S, Duong M N. 1986. Superoxide dismutase and oxygen toxicity defenses in the genus *Neisseria*. Infect Immun 51(2):631-41.

Aspholm M, Aas F E, Harrison O B, Quinn D, Vik A, Viburiene R, Tonjum T, Moir J, Maiden M C, Koomey M. 2010. Structural alterations in a component of cytochrome c oxidase and molecular evolution of pathogenic *Neisseria* in humans. PLoS Pathog 6(8):e1001055.

Baart G J, de Jong G, Philippi M, van't Riet K, van der Pol L A, Beuvery E C, Tramper J, Martens D E. 2007a. Scale-up for bulk production of vaccine against meningococcal disease. Vaccine 25(34):6399-408.

Baart G J, Zomer B, de Haan A, van der Pol L A, Beuvery E C, Tramper J, Martens D E. 2007b. Modeling *Neisseria meningitidis* metabolism: from genome to metabolic fluxes. Genome Biol 8(7):R136.

Baez A, Shiloach J. 2014. Effect of elevated oxygen concentration on bacteria, yeasts, and cells propagated for production of biological compounds. Microb Cell Fact 13(1):181.

Bernadac A, Gavioli M, Lazzaroni J C, Raina S, Lloubes R. 1998. *Escherichia coli* tol-pal mutants form outer membrane vesicles. J Bacteriol 180(18):4872-8.

Bøvre K. 1984. Neisseriaceae Prevot 1933. In: N. R. Krieg & J. G. Hold, editor. Bergey's manual of systemic bacteriology. Baltimore, Md.: Williams and Wilkin.

Brandtzaeg P, Kierulf P, Gaustad P, Skulberg A, Bruun J N, Halvorsen S, Sorensen E. 1989. Plasma endotoxin as a predictor of multiple organ failure and death in systemic meningococcal disease. J Infect Dis 159(2):195-204.

Claassen I, Meylis J, van der Ley P, Peeters C, Brons H, Robert J, Borsboom D, van der Ark A, van Straaten I, Roholl P and others. 1996. Production, characterization and control of a *Neisseria meningitidis* hexavalent class 1 outer membrane protein containing vesicle vaccine. Vaccine 14(10):1001-8.

Deatherage B L, Lara J C, Bergsbaken T, Rassoulian Barrett S L, Lara S, Cookson B T. 2009. Biogenesis of bacterial membrane vesicles. Mol Microbiol 72(6):1395-407.

Deeudom M, Koomey M, Moir J W. 2008. Roles of c-type cytochromes in respiration in *Neisseria meningitidis*. Microbiology 154(Pt 9):2857-64.

Dorward D W, Garon C F. 1990. DNA Is Packaged within Membrane-Derived Vesicles of Gram-Negative but Not Gram-Positive Bacteria. Appl Environ Microbiol 56(6):1960-2.

Ellen A F, Albers S V, Huibers W, Pitcher A, Hobel C F, Schwarz H, Folea M, Schouten S, Boekema E J, Poolman B and others. 2009. Proteomic analysis of secreted membrane vesicles of archaeal *Sulfolobus* species reveals the presence of endosome sorting complex components. Extremophiles 13(1):67-79.

Espesset D, Corda Y, Cunningham K, Bénédetti H, Lloubès R, Lazdunski C, Géli V. 1994. The colicin A pore-forming domain fused to mitochondrial intermembrane space sorting signals can be functionally inserted into the *Escherichia coli* plasma membrane by a mechanism that bypasses the Tol proteins. Molecular Microbiology 13(6):1121-1131.

Fredriksen J H, Rosenqvist E, Wedege E, Bryn K, Bjune G, Froholm L O, Lindbak A K, Mogster B, Namork E, Rye U and others. 1991. Production, characterization and control of MenB-vaccine "Folkehelsa": an outer membrane vesicle vaccine against group B meningococcal disease. NIPH Ann 14(2):67-79; discussion 79-80.

Gerritzen M J H, Martens D E, Wijffels R H, Stork M. 2017. High throughput nanoparticle tracking analysis for monitoring outer membrane vesicle production. J Extracell Vesicles 6(1):1333883.

Gorringe A R, Pajon R. 2012. Bexsero: a multicomponent vaccine for prevention of meningococcal disease. Hum Vaccin Immunother 8(2):174-83.

Haugaard N. 1968. Cellular mechanisms of oxygen toxicity. Physiol Rev 48(2):311-73.

Haurat M F, Elhenawy W, Feldman M F. 2015. Prokaryotic membrane vesicles: new insights on biogenesis and biological roles. Biol Chem 396(2):95-109.

Hewitt C J, Nebe-Von Caron G, Axelsson B, McFarlane C M, Nienow A W. 2000. Studies related to the scale-up of high-cell-density *E. coli* fed-batch fermentations using multiparameter flow cytometry: effect of a changing microenvironment with respect to glucose and dissolved oxygen concentration. Biotechnol Bioeng 70(4):381-90.

Holst J, Martin D, Arnold R, Huergo C C, Oster P, O'Hallahan J, Rosenqvist E. 2009. Properties and clinical performance of vaccines containing outer membrane vesicles from *Neisseria meningitidis*. Vaccine 27 Suppl 2:B3-12.

Holten E. 1979. Serotypes of *Neisseria meningitidis* isolated from patients in Norway during the first six months of 1978. J Clin Microbiol 9(2):186-8.

Imlay J A. 2008. Cellular defenses against superoxide and hydrogen peroxide. Annu Rev Biochem 77:755-76.

Korshunov S, Imlay J A. 2006. Detection and quantification of superoxide formed within the periplasm of *Escherichia coli*. J Bacteriol 188(17):6326-34.

Kulp A, Kuehn M J. 2010. Biological functions and biogenesis of secreted bacterial outer membrane vesicles. Annu Rev Microbiol 64:163-84.

Lappann M, Danhof S, Guenther F, Olivares-Florez S, Mordhorst I L, Vogel U. 2013a. In vitro resistance mechanisms of *Neisseria meningitidis* against neutrophil extracellular traps. Mol Microbiol 89(3):433-49.

Lappann M, Otto A, Becher D, Vogel U. 2013b. Comparative proteome analysis of spontaneous outer membrane vesicles and purified outer membranes of *Neisseria meningitidis*. J Bacteriol 195(19):4425-35.

Li Y, Hopper A, Overton T, Squire D J, Cole J, Tovell N. 2010. Organization of the electron transfer chain to oxygen in the obligate human pathogen *Neisseria gonorrhoeae*: roles for cytochromes c4 and c5, but not cytochrome c2, in oxygen reduction. J Bacteriol 192(9):2395-406.

Malloy A, Carr B. 2006. NanoParticle Tracking Analysis—The Halo™ System. Particle & Particle Systems Characterization 23(2):197-204.

Malvern Instruments. 2015. NanoSight NTA Concentration Measurement Upgrade.

Metz B, Hoonakker M, Uittenbogaard J P, Weyts M, Mommen G P, Meiring H D, Tilstra W, Pennings J L, van der Pol L A, Kuipers B and others. 2017. Proteome Analysis Is a Valuable Tool to Monitor Antigen Expression during Upstream Processing of Whole-Cell Pertussis Vaccines. J Proteome Res 16(2):528-537.

Moslen M T. 1994. Reactive oxygen species in normal physiology, cell injury and phagocytosis. Adv Exp Med Biol 366:17-27.

Ng V H, Cox J S, Sousa A O, MacMicking J D, McKinney J D. 2004. Role of KatG catalase-peroxidase in mycobacterial pathogenesis: countering the phagocyte oxidative burst. Mol Microbiol 52(5):1291-302.

Paalme T, Kahru A, Elken R, Vanatalu K, Tiisma K, Raivo V. 1995. The computer-controlled continuous culture of *Escherichia coli* with smooth change of dilution rate (A-stat). Journal of Microbiological Methods 24(2):145-153.

Pathirana R D, Kaparakis-Liaskos M. 2016. Bacterial membrane vesicles: Biogenesis, immune regulation and pathogenesis. Cell Microbiol 18(11):1518-1524.

Port J L, DeVoe I W, Archibald F S. 1984. Sulphur acquisition by *Neisseria meningitidis*. Can J Microbiol 30(12):1453-7.

Raeven R H, van der Maas L, Tilstra W, Uittenbogaard J P, Bindels T H, Kuipers B, van der Ark A, Pennings J L, van Riet E, Jiskoot W and others. 2015. Immunoproteomic Profiling of *Bordetella pertussis* Outer Membrane Vesicle Vaccine Reveals Broad and Balanced Humoral Immunogenicity. J Proteome Res 14(7):2929-42.

Rivera J, Cordero R J, Nakouzi A S, Frases S, Nicola A, Casadevall A. 2010. *Bacillus anthracis* produces membrane-derived vesicles containing biologically active toxins. Proc Natl Acad Sci USA 107(44):19002-7.

Roier S, Zingl F G, Cakar F, Durakovic S, Kohl P, Eichmann T O, Klug L, Gadermaier B, Weinzerl K, Prassl R and others. 2016. A novel mechanism for the biogenesis of outer membrane vesicles in Gram-negative bacteria. Nat Commun 7:10515.

Sabra W, Lunsdorf H, Zeng A P. 2003. Alterations in the formation of lipopolysaccharide and membrane vesicles on the surface of *Pseudomonas aeruginosa* PAO1 under oxygen stress conditions. Microbiology 149(Pt 10):2789-95.

Schwechheimer C, Kuehn M J. 2015. Outer-membrane vesicles from Gram-negative bacteria: biogenesis and functions. Nat Rev Microbiol 13(10):605-19.

Schwechheimer C, Sullivan C J, Kuehn M J. 2013. Envelope control of outer membrane vesicle production in Gram-negative bacteria. Biochemistry 52(18):3031-40.

Seib K L, Tseng H J, McEwan A G, Apicella M A, Jennings M P. 2004. Defenses against oxidative stress in *Neisseria gonorrhoeae* and *Neisseria meningitidis*: distinctive systems for different lifestyles. J Infect Dis 190(1):136-47.

Seib K L, Wu H J, Kidd S P, Apicella M A, Jennings M P, McEwan A G. 2006. Defenses against oxidative stress in *Neisseria gonorrhoeae*: a system tailored for a challenging environment. Microbiol Mol Biol Rev 70(2):344-61.

Steeghs L, van Vliet S J, Uronen-Hansson H, van Mourik A, Engering A, Sanchez-Hernandez M, Klein N, Callard R, van Putten J P, van der Ley P and others. 2006. *Neisseria meningitidis* expressing lgtB lipopolysaccharide targets DC-SIGN and modulates dendritic cell function. Cell Microbiol 8(2):316-25.

Storz G, Imlay J A. 1999. Oxidative stress. Curr Opin Microbiol 2(2):188-94.

Su F H, Tabañag I D F, Wu C Y, Tsai S L. 2017. Decorating outer membrane vesicles with organophosphorus hydrolase and cellulose binding domain for organophosphate pesticide degradation. Chemical Engineering Journal 308:1-7.

Thalen M, van den I J, Jiskoot W, Zomer B, Roholl P, de Gooijer C, Beuvery C, Tramper J. 1999. Rational medium design for *Bordetella pertussis*: basic metabolism. J Biotechnol 75(2-3):147-59.

Tommassen J, Vermeij P, Struyve M, Benz R, Poolman J T. 1990. Isolation of *Neisseria meningitidis* mutants deficient in class 1 (porA) and class 3 (porB) outer membrane proteins. Infect Immun 58(5):1355-9.

Tseng H J, Srikhanta Y, McEwan A G, Jennings M P. 2001. Accumulation of manganese in *Neisseria gonorrhoeae* correlates with resistance to oxidative killing by superoxide anion and is independent of superoxide dismutase activity. Mol Microbiol 40(5):1175-86.

van de Waterbeemd B, Mommen G P, Pennings J L, Eppink M H, Wijffels R H, van der Pol L A, de Jong A P. 2013a. Quantitative proteomics reveals distinct differences in the protein content of outer membrane vesicle vaccines. J Proteome Res 12(4):1898-908.

van de Waterbeemd B, Streefland M, van der Ley P, Zomer B, van Dijken H, Martens D, Wijffels R, van der Pol L. 2010. Improved OMV vaccine against *Neisseria meningitidis* using genetically engineered strains and a detergent-free purification process. Vaccine 28(30):4810-6.

van de Waterbeemd B, Zomer G, van den Ijssel J, van Keulen L, Eppink M H, van der Ley P, van der Pol L A. 2013b. Cysteine depletion causes oxidative stress and triggers outer membrane vesicle release by *Neisseria meningitidis*: implications for vaccine development. PLoS One 8(1):e54314.

van der Ley P, Steeghs L, Hamstra H J, ten Hove J, Zomer B, van Alphen L. 2001. Modification of lipid A biosynthesis in *Neisseria meningitidis* lpxL mutants: influence on lipopolysaccharide structure, toxicity, and adjuvant activity. Infect Immun 69(10):5981-90.

van Deuren M, van der Ven-Jongekrijg J, Bartelink A K, van Dalen R, Sauerwein R W, van der Meer J W. 1995. Correlation between proinflammatory cytokines and anti-inflammatory mediators and the severity of disease in meningococcal infections. J Infect Dis 172(2):433-9.

van Hemert P A. 1967. Specific properties of acid precipitated pertussis vaccine. Prog Immunobiol Stand 3:297-301.

Zariri A, van der Ley P. 2015. Biosynthetically engineered lipopolysaccharide as vaccine adjuvant. Expert Rev Vaccines 14(6):861-76.

Zollinger W D, Mandrell R E, Griffiss J M, Altieri P, Berman S. 1979. Complex of meningococcal group B polysaccharide and type 2 outer membrane protein immunogenic in man. J Clin Invest 63(5):836-48.

The invention claimed is:

1. A process for producing spontaneously released bacterial outer membrane vesicles (OMV), wherein the process comprises the steps of:
   a) cultivating a population of a Gram-negative bacterium, which cultivation comprises stimulation of the release of OMV by application of a dissolved oxygen tension (DOT) that is higher than a physiological DOT of 40% air saturation measured at 35° C.; and, b) recovering the OMV released in a), wherein the recovery at least comprises removal of the bacteria from the OMV.

2. The process according to claim 1, wherein the DOT applied to stimulate the release of OMV is at least 50, 55, 60, 70, 80, 90, 100, 125, 150 or 200% air saturation measured at 35° C.

3. The process according to claim 1, wherein said cultivating comprises a mode that employs adding a feeding medium, wherein said mode is selected from fed-batch mode, semi-continuous mode, and continuous mode.

4. The process according to claim 1, wherein the process comprises:
   a) a first phase wherein biomass of the Gram-negative bacterium is accumulated at a first DOT; and,
   b) a second phase wherein release of OMV from the biomass accumulated in a) is stimulated by the application of a second DOT that is higher than the first DOT.

5. The process according to claim 1, wherein the Gram-negative bacterium has at least one of:
   a) a genetic modification which causes the bacterium to produce an LPS with reduced toxicity but which LPS retains at least part of its adjuvant activity;
   b) a genetic modification which causes the bacterium to overproduce OMV as compared to a corresponding wild-type bacterium without the genetic modification, wherein the genetic modification is a modification that attenuates the peptidoglycan-binding activity of one or more proteins comprising a peptidoglycan-associated site; and
   c) a genetic modification that decreases or knocks-out expression of a gene product, and wherein the gene product is selected from the group consisting of cps, a lipid A biosynthesis gene product, PorA, PorB and opA.

6. The process according to claim 1, wherein the Gram-negative bacterium belongs to a genus selected from the group consisting of the genera *Neisseria, Bordetella, Helicobacter, Salmonella, Vibrio, Shigella, Haemophilus, Pseudomonas, Escherichia, Moraxella, Klebsiella* and *Acinetobacter*.

7. The process according to claim 1, wherein the Gram-negative bacterium expresses an antigen foreign to said Gram-negative bacterium.

8. The process according to claim 1, wherein the Gram-negative bacterium expresses multiple antigens.

9. The process according to claim 1, wherein the OMV are sterilized.

10. The process according to claim 1, further comprising the step of combining the OMV with a pharmaceutically accepted excipient and optionally an adjuvant.

11. The process according to claim 1, wherein the wherein the process comprises incorporating the OMV into a vaccine composition.

12. The process according to claim 1, wherein the DOT applied to stimulate the release of OMV is less than 350, 325, 300, 275, 250, 225, 205 or 185% air saturation measured at 35° C.

13. The process according to claim 4, wherein the first DOT is a physiological DOT.

14. The process according to claim 13, wherein the physiological DOT is a DOT of less than 50, 40, 35 or 32% air saturation measured at 35° C.

15. The process according to claim 5, wherein the Gram-negative bacterium has at least one of:
  a) the genetic modification which causes the bacterium to produce an LPS with reduced toxicity but which LPS retains at least part of its adjuvant activity, wherein the modification is a modification that decreases or knocks-out expression of one or more genes selected from the lpxL1 and lpxL2 genes or homologues thereof and the lpxK gene or a homologue thereof and/or is a modification that effects the expression of one or more lpxE and/or pagL genes; and
  b) the genetic modification which causes the bacterium to overproduce OMV as compared to a corresponding wild-type bacterium without the genetic modification, wherein the modification is a modification that decreases or knocks-out expression of one or more genes selected from the group consisting of the tolQ, tolR, tolA, tolB, tolRA, rmpM and ompA genes.

16. The process according to claim 6, wherein the Gram-negative bacterium is of a species selected from the group consisting of *Neisseria meningitidis, Neisseria lactamica, Neisseria gonorrhoeae, Helicobacter pylori, Salmonella typhi, Salmonella typhimurium, Vibrio cholerae, Shigella* spp., *Haemophilus influenzae, Bordetella pertussis, Pseudomonas aeruginosa, Escherischia coli, Moraxella catarrhalis, Klebsiella pneumoniae* and *Acinetobacter baumannii*.

17. The process according to claim 1, wherein the Gram-negative bacterium population comprises more than one strain of the Gram-negative bacterium, and wherein each strain expresses different antigens.

18. The process according to claim 1, wherein the OMV are sterilized by filter sterilization.

19. The process according to claim 2 wherein the OMV are sterilized by filter sterilization using a filter with pores of less than about 0.3 micrometer.

* * * * *